United States Patent
Tomioka et al.

(10) Patent No.: US 6,972,080 B1
(45) Date of Patent: Dec. 6, 2005

(54) ELECTROCHEMICAL DEVICE FOR MOVING PARTICLES COVERED WITH PROTEIN

(75) Inventors: Toshikazu Tomioka, Ibaraki (JP); Akira Ryoji, Osaka (JP); Tomoe Ono, Osaka (JP); Hiroaki Yoshida, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 297 days.

(21) Appl. No.: 09/762,519

(22) PCT Filed: Jun. 12, 2000

(86) PCT No.: PCT/JP00/03789

§ 371 (c)(1),
(2), (4) Date: Feb. 7, 2001

(87) PCT Pub. No.: WO00/77163

PCT Pub. Date: Dec. 21, 2000

(30) Foreign Application Priority Data

| Jun. 10, 1999 | (JP) | ................................. 11-163518 |
| Jul. 7, 1999 | (JP) | ................................. 11-193255 |
| Jul. 19, 1999 | (JP) | ................................. 11-204148 |
| Sep. 14, 1999 | (JP) | ................................. 11-261097 |
| May 23, 2000 | (JP) | ................................. 2000-150960 |

(51) Int. Cl.[7] ......................................... G01N 27/447
(52) U.S. Cl. .......................... 204/600; 204/450; 429/2
(58) Field of Search ............................... 204/600, 627, 204/639, 641, 648, 550; 429/2; 422/44, 255; 435/308.1

(56) References Cited

U.S. PATENT DOCUMENTS

| 3,865,711 A | * | 2/1975 | Anderson .................... 204/600 |
| 4,767,401 A | * | 8/1988 | Seiderman ................... 604/20 |
| 4,927,408 A | * | 5/1990 | Haak et al. ................... 604/20 |
| 5,858,192 A | | 1/1999 | Becker et al. |
| 5,944,685 A | * | 8/1999 | Muroki ........................ 604/20 |
| 6,129,696 A | * | 10/2000 | Sibalis ......................... 604/20 |
| 6,334,856 B1 | * | 1/2002 | Allen et al. .................. 604/191 |
| 6,522,918 B1 | * | 2/2003 | Crisp et al. ................... 604/20 |

FOREIGN PATENT DOCUMENTS

| JP | 60-188836 | 9/1985 |
| JP | 4-127049 | 4/1992 |
| JP | 08-101163 A | 4/1996 |
| JP | 11057459 A | 3/1999 |
| WO | WO 96/31282 A1 | 10/1996 |
| WO | WO 98/10869 A1 | 3/1998 |

OTHER PUBLICATIONS

"Food Batteries," at http://www.madsci.org/experiments/archive/889917606.Ch.html (Narch 14, 1998).*

* cited by examiner

*Primary Examiner*—Nam Nguyen
*Assistant Examiner*—Jeffrey Barton
(74) *Attorney, Agent, or Firm*—Akin Gump Strauss Hauer & Feld, LLP

(57) ABSTRACT

An electrochemical device for moving particles covered with a protein is provided. The device includes at least two electrodes that are in contact with a liquid containing the protein-covered particles and a circuit that generates a potential difference in a range that does not cause electrolysis of the liquid between the electrodes. The particles are moved by electrophoresis in the direction of the arrangement of the electrodes. The invention provided herein has numerous applications, including use in a microorganism concentration condensing device, a blood component induction device, and/or a blood component induction method, and/or an electric appliance that decreases the concentration of microorganisms present on the surface of a heat exchanger.

3 Claims, 13 Drawing Sheets

US 6,972,080 B1

ELECTROCHEMICAL DEVICE FOR MOVING PARTICLES COVERED WITH PROTEIN

This application is a national stage entry of International Patent Application No. PCT/JP00/03789, filed on Jun. 12, 2000, and which claims priority to Japanese Patent Applications 11-163518, filed Jun. 10, 1999; 11-193255, filed Jul. 7, 1999; 11-204148, filed Jul. 19, 1999; 11-261097, filed Sep. 14, 1999; and 2000-150960, filed May 23, 2000.

TECHNICAL FIELD

The present invention relates to an electrochemical device for moving particles covered with a protein, such as a microorganism and a blood cell component.

BACKGROUND ART

Numerous improvements have been carried out conventionally for detection of a microorganism. The most important improvement is the enhancement of detection sensitivity. However, a difference is still present between the concentration at which harm to the human being by a microorganism is recognized and detection sensitivity; and further enhancement of detection sensitivity is required. Toward this, methods for enhancing detection sensitivity by condensing the concentration of a microorganism in a test liquid for example have been examined. Among these methods, the most prevalent method is a method of condensing the concentration of a microorganism by filtration and re-dispersion.

However, there are some microorganisms which are adsorbed by a filtering material and do not re-extracted at the time of re-dispersion, and this causes a problem of being difficult to quantitatively determine these microorganisms. In addition, in the above-mentioned technical field, it is desired to have a technology for condensing the concentration of a microorganism at higher quantity in a period shorter than the proliferation time of the microorganism by a simple procedure at low cost. Furthermore, regarding the waste treatment of a material, which is used at the time of condensation, it is also desired to have the material being low in cost, easy to use and hard to pollute environment at the time of disposal.

Furthermore, numerous improvements have been carried out conventionally for the removal of microorganisms (bacteria removal) included in a blood sample, and a method called disinfection using a drug has been adopted for this bacteria removal in general.

However, blood itself is a liquid including much nourishment and functions as a medium for microorganisms; the disinfection method therefore causes various problems. For example, there is a limitation in the rate of disinfection, and the use of the drug may cause a harmful side effect. Regarding the harmful side effect of the drug in particular, if each bacteria gains resistance against a disinfectant, hospital-spread infection and the like may occur via blood, and this gives rise to a need for development of a newer disinfectant. In other words, the development of a disinfectant must be repeatedly competed with the gaining of the resistance against the disinfectant by bacteria, resulting in a social problem of today.

In addition, in an electric appliance, such as an air conditioner, numerous examinations have been carried out for the microorganisms included in the air discharged into a room. Various ideas have been proposed and embodied, in which, for example, a filter is provided in the airflow passage of the air conditioner to capture microorganisms included in the air, and an antimicrobial agent is disposed on the surface of the filter to restrict the activity of the captured microorganisms.

However, inorganic and organic components evaporating and dissipating from an organism and suspending organic components are present in the air together with microorganisms, and these may become nourishment sources for the microorganisms. In other words, when sweat, carbon dioxide and nitrogen compounds such as ammonia components, in the air enter the interior of the air conditioner, they are captured by condensed dew water on the surface of the heat exchanger in which dew formation occurred. On the other hand, suspending microorganisms also adhere to the surface of the heat exchanger in the same manner. Since the heat exchanger is controlled to operate and stop repeatedly depending on the ambient temperature, it becomes wet and dry repeatedly. In addition, while the air conditioner is repeatedly operated and stopped in a cycle of one day, the above-mentioned adhered microorganisms may proliferate by virtue of the captured nourishment sources. Furthermore, if the dry state of the heat exchanger is maintained, the affinity of the proliferated microorganisms to the surface of the heat exchanger may become less, and they may scatter in the air again.

Furthermore, a refrigerator also has a heat exchanger in the interior like the air conditioner, and microorganisms scattered from food accommodated in the interior adhere to the surface of the heat exchanger. As a result, the microorganisms multiply depending on the temperature of the surface of the heat exchanger during the thawing cycle and the like, and may contaminate the interior of the refrigerator again. It is therefore required to reduce the microorganisms on the surface of the heat exchanger and to keep the surface clean.

As described above, the existence of particles covered with a protein such as microorganisms and blood cell components has conventionally been an important factor in condensing a solution to be detected, in adjusting a blood component and in removing bacteria from air conditioners.

Accordingly, the present invention is intended to provide an electrochemical device capable of moving such particles by using a simple method.

More particularly, the present invention is intended to provide a microorganism concentration condensing device capable of condensing the concentration of a microorganism in a test liquid including the microorganism, a bacteria removal device, a blood component induction device and a blood component induction method capable of separating a blood component from a blood sample and/or capable of physically removing a microorganism from a blood sample, and an electric appliance capable of decreasing the concentration of a microorganism on the surface of a heat exchanger.

DISCLOSURE OF INVENTION

The present invention relates to an electrochemical device for moving particles covered with a protein, characterized in that said device has at least n (n≧2) pieces of electrodes contacting with a liquid containing particles covered with a protein and a circuit generating a potential difference between the above-mentioned electrodes in a range such that it does not cause the electrolysis of the above-mentioned liquid, said device allowing the above-mentioned particles move by electrophoresis in the aligned direction of the above-mentioned electrodes.

In this electrochemical device, it is effective that the above-mentioned circuit is a circuit sweepingly-applies a voltage in a range such that it does not cause the electrolysis of the above-mentioned liquid to the above-mentioned n pieces of electrodes sequentially in a constant direction, and moves the above-mentioned particles by electrophoresis in the above-mentioned direction.

In addition, it is effective that the above-mentioned particles covered with a protein are microorganisms and/or blood cell components, and that a liquid having a condensed concentration of the microorganisms and/or blood cell components is obtained.

Furthermore, it is effective that the device has a structure allowing the above-mentioned liquid flow across the above-mentioned electrodes, and that the direction of voltage application to the respective electrodes is perpendicular to the flow direction of the above-mentioned liquid.

Furthermore, it is effective that the above-mentioned electrodes are vortex-type electrodes, and that the above-mentioned electrodes are disposed so as to extend to the same central point from the outer end portions to the inner end portions of the above-mentioned electrodes without overlapping each other.

Furthermore, it is effective that the above-mentioned electrodes are spiral electrodes, and that the above-mentioned electrodes are disposed so as to extend from the upper end portions to the lower end portions of the above-mentioned electrodes without overlapping each other.

Furthermore, it is effective that the above-mentioned electrodes are sheet-shaped porous electrodes and that the device is provided with a wound type electrode, which is obtained by stacking n (n≧3) pieces of laminates, each comprising the above-mentioned sheet-shaped porous electrode and a sheet-shaped porous spacer in the order of the above-mentioned electrode and spacer and by winding the stacked laminates.

Furthermore, in the above-mentioned electrochemical device, it is effective that the above-mentioned n pieces of electrodes have oxidation/reduction potentials different from each other, and the above-mentioned circuit is one short-circuiting the above-mentioned n pieces of electrodes to move the above-mentioned particles by electrophoresis in the aligned direction of the above-mentioned electrodes.

In this case, it is effective that the above-mentioned particles covered with a protein are microorganisms and/or blood cell components, and that a liquid having a condensed concentration of the microorganisms and/or blood cell components is obtained.

Furthermore, it is effective that an introduction portion and a discharge portion for the above-mentioned liquid are provided in the vicinity of an electrode having a higher oxidation/reduction potential, and that a microorganism discharge portion and/or a microorganism adsorption portion are provided in the vicinity of an electrode having a lower oxidation/reduction potential.

Furthermore, it is effective that an electrically insulating structural member through which the above-mentioned liquid can move is disposed in the space between the above-mentioned electrodes.

Furthermore, it is effective that an electrode other than electrode(s) having the lowest oxidation/reduction potential has a structure allowing the above-mentioned liquid to flow into the above-mentioned space.

Furthermore, it is effective that the above-mentioned structure has a porous, mesh or brush form.

Furthermore, it is effective that an electrode other than electrode(s) having the lowest oxidation/reduction potential has the form of a film, through which the microorganisms and/or blood cell components contained in the above-mentioned liquid transmit, and is stacked on the surface of the above-mentioned electrically insulating structural member.

BEST MODE FOR CARRYING OUT THE INVENTION

Figure 1:
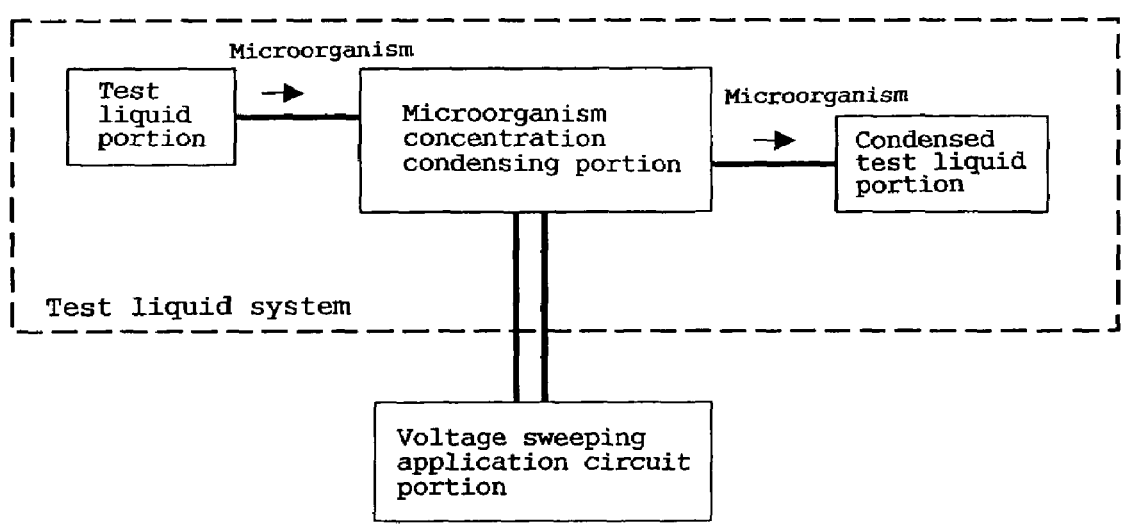
FIG. 1 is a block diagram showing the structure of a microorganism concentration condensing device in accordance with the present invention.

The inventors of the present invention paid attention to the fact that particles covered with a protein such as microorganisms and blood cell components have certain charges because of the protein and completed the present invention. Namely, the present invention relates to an electrochemical device for moving particles covered with a protein, comprising at least n (n≧2) pieces of electrodes contacting with a liquid containing particles covered with a protein and a circuit generating a potential difference in a range such that it does not cause the electrolysis of the above-mentioned liquid between the above-mentioned electrodes, wherein the above-mentioned particles are moved by electrophoresis.

The above-mentioned particles covered with a protein may be contained in the above-mentioned liquid in any state, such as a dispersion or a suspension. As the above-mentioned particles, there are exemplified microorganisms and/or blood cell components. For this reason, a solvent, an electrolyte and the like may also be contained in the above-mentioned liquid.

In the case where this electrochemical device is applied to an electric appliance provided with a heat exchanger, the present invention provides an electric appliance provided with a heat exchanger, comprising an opposed member opposed to the heat exchanger with a space therebetween and disposed in condensed dew water flowing from the above-mentioned heat exchanger at a position contacting with the above-mentioned condensed dew water together with the surface of the above-mentioned heat exchanger, in which a microorganism present between the above-mentioned heat exchanger and the above-mentioned opposed member is moved in the direction of the above-mentioned opposed member.

The electrochemical device of the present invention can be applied further to various devices. In particular, by changing the type of the electrode and the structure of the circuit, it is possible to obtain electrochemical devices, which operates by using mainly two kinds of mechanisms.

More specifically, the present invention provides a first electrochemical device comprising plural electrodes having the same oxidation/reduction potential and a circuit capable of sweepingly applying a voltage to the plural electrodes, and a second electrochemical device comprising plural electrodes having different oxidation/reduction potentials and a circuit short-circuiting the above-mentioned plural electrodes. In the second electrochemical device in particular, the inventors of the present invention have found that if the plural electrodes having different oxidation/reduction potentials are employed, the above-mentioned particles can be moved by simply short-circuiting the electrodes even without positively applying a voltage.

Still more specifically, the present invention can be used as a microorganism concentration condensing device, a bacteria removing device and a blood component inducting device having various functions and shapes by appropriately changing the kind of the above-mentioned particle and liquid, the number and kind of the electrode and the configuration of the circuit.

The above-mentioned first electrochemical device and second electrochemical device will be described below.

(1) With Respect to First Electrochemical Device (i) Microorganism Concentration Condensing Device The present invention provides a microorganism concentration condensing device comprising at least n (n≧3) pieces of electrodes contacting with a test liquid containing a microorganism, a substrate with the above-mentioned electrodes disposed thereon, and a circuit sweepingly applying a voltage in a range such that it does not cause the electrolysis of the above-mentioned test liquid to the above-mentioned respective electrodes sequentially in a constant direction to move the microorganisms in the above-mentioned test liquid by electrophoresis to obtain a test liquid having a high microorganism concentration.

In this microorganism concentration condensing device, it is effective that the above-mentioned electrodes are vortex-type electrodes, that the above-mentioned substrate is a flat substrate, and that the above-mentioned electrodes are disposed on the above-mentioned flat portion so as to extend to the same central point from the outer end portions to the inner end portions of the above-mentioned electrodes without overlapping each other.

Furthermore, it is effective that the above-mentioned electrodes are spiral electrodes, that the above-mentioned substrate is a pillar-shaped substrate, and that the above-mentioned electrodes are disposed on the side of the above-mentioned pillar-shaped portion so as to extend from the upper end portions to the lower end portions of the above-mentioned electrodes without overlapping each other.

Furthermore, it is effective that the above-mentioned electrodes are sheet-shaped porous electrodes, that the above-mentioned substrate is a sheet-shaped porous spacer, that n (n≧3) pieces of laminates, each comprising the above-mentioned sheet-shaped electrode and the porous spacer, are stacked in the order of the above-mentioned electrode and spacer without overlapping at the end portions of the electrodes of the respective laminates, and that the laminates are wound.

Furthermore, it is effective that the above-mentioned circuit performs sweeping application by applying a positive voltage for microorganism migration to the first electrode of the above-mentioned n pieces of electrodes, applying a negative voltage for microorganism migration to the above-mentioned first electrode at the same time when applying a positive voltage for microorganism migration to the second electrode, applying a negative voltage for microorganism migration to the (n−1)th to the first electrodes at the same time when applying a positive voltage for microorganism migration to the "n"th electrode, furthermore, applying a negative voltage for microorganism migration to the "n"th to the second electrodes at the same time when applying a positive voltage for microorganism migration to the above-mentioned first electrode, whereby the microorganism are allowed to migrate from the first electrode to the "n"th electrode.

Furthermore, it is effective that the above-mentioned circuit sweepingly applies a voltage to the above-mentioned electrodes at a rate of 100 μm/sec or less in terms of the distance of the migration of the microorganism.

A plurality of the above-mentioned substrates having the electrodes may be provided. In addition, the above-mentioned electrodes may form paired electrodes.

The above-mentioned microorganism concentration condensing device comprises at least n (n≧3) pieces of electrodes contacting with a test liquid containing a microorganism, a substrate with the above-mentioned electrodes disposed thereon, and a circuit sweepingly applying a voltage in a range such that it doe not cause the electrolysis of the above-mentioned test liquid to the above-mentioned electrodes sequentially in a constant direction, whereby the microorganism in the above-mentioned test liquid is moved on the above-mentioned substrate and a test liquid having a high microorganism concentration can be given.

This microorganism concentration condensing device may be used to detect the concentration of the microorganism contained in the test liquid, and may be used for a part of a microorganism concentration measurement system. Herein, FIG. 1 is a block diagram conceptually showing the structure of the microorganism concentration condensing device in accordance with the present invention. As shown in FIG. 1, the microorganism concentration condensing device in accordance with the present invention comprises a test liquid system comprising a test liquid portion, a condensed test liquid portion and a microorganism concentration condensing portion, and a circuit portion for sweepingly applying a voltage to the electrodes of the microorganism concentration condensing portion.

The number of the electrodes is not limited in particular, provided that the number is three or more. In the followings, the operation principle of the microorganism concentration condensing device of the present invention will be described by taking a case in which the number of the electrodes is three as a typical example.

In first, a voltage having a level not electrolyzing the test liquid, particularly an electrolyte contained in the test liquid, is applied to the electrodes arranged in accordance with the above-mentioned structure. This voltage having a level not electrolyzing the test liquid should be determined depending on the electrode, the solvent containing a microorganism, the electrolyte and medium for proliferation and the like.

By applying the voltage as described above, the negatively charged microorganism can be moved by electrophoresis without causing deterioration of the test liquid due to the electrolysis. In other words, by making one of the electrodes negative and by making the other positive, the microorganism can be allowed to migrate from the negative portion to the positive portion. As a result, it is possible to obtain a test liquid having a condensed concentration.

Figure 2:
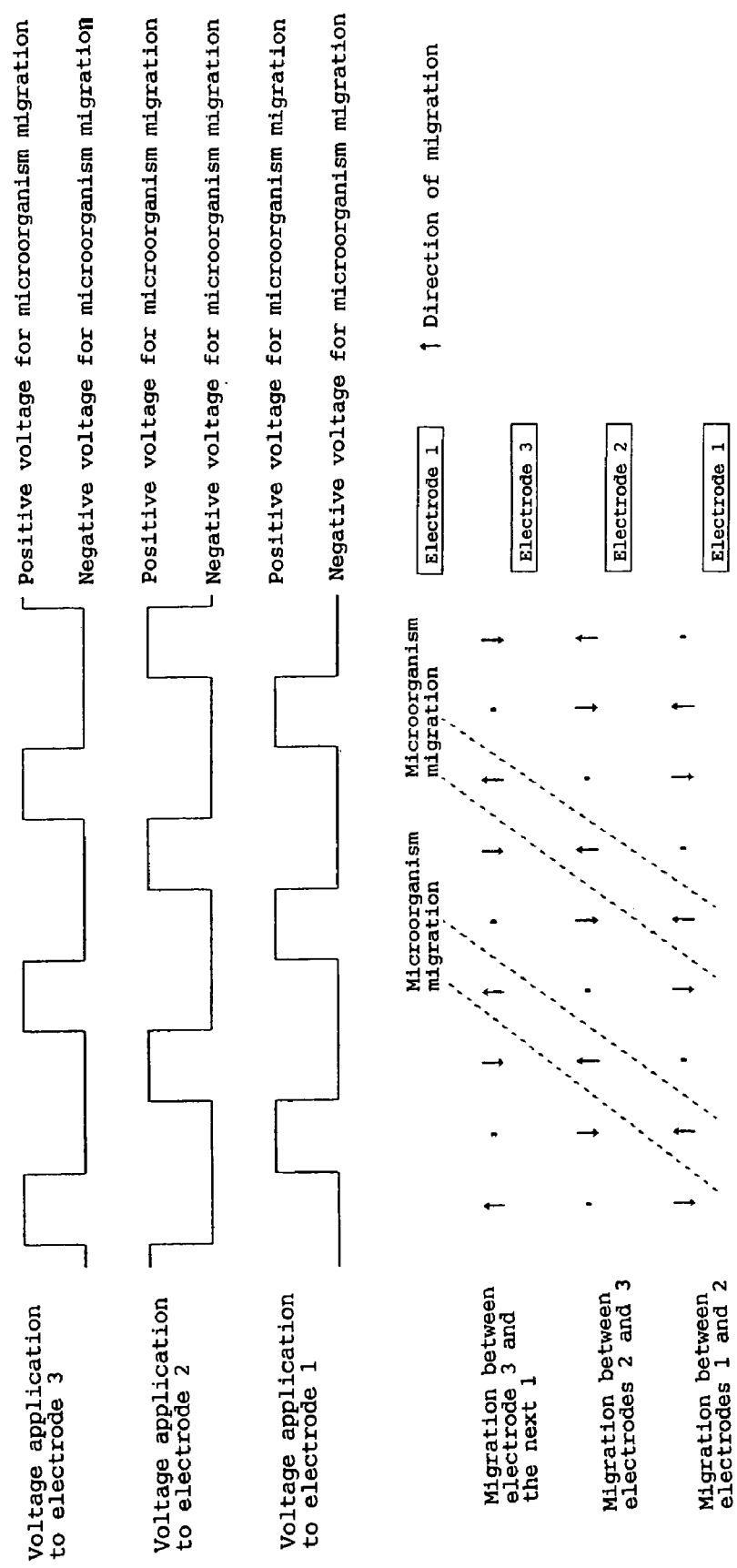
FIG. 2 is a view showing a method of sweepingly applying voltage to respective electrodes using a circuit in the microorganism concentration condensing device in accordance with the present invention.

The method of the voltage application to each electrode will be described in more detail. It is preferable that voltage application is carried out sequentially at constant intervals in order that the microorganism is allowed to migrate in a constant direction along each electrode. It is therefore preferable to apply a pulse-shaped potential. FIG. 2 is a view showing a method of sweepingly applying voltage to the respective electrodes by using a circuit in the concentration condensing device in accordance with the present invention.

The electrodes are arranged sequentially in the migration direction of microorganism, a first electrode, a second electrode and a third electrode; the voltage is applied to the electrodes in the order of the first electrode, the second electrode and the third electrode; hereafter, the voltage is applied again to the first electrode, the second electrode and the third electrode sequentially and repeatedly.

The duration of time between voltage application to one electrode and voltage application to the next electrode, i.e., the rate of sweeping, differs depending on the distance between the electrodes, the thickness of the electrodes, and the like; however, the rate is required to be substantially less than the rate of the migrating microorganism. As a result of experiments, the inventors of the present invention have found that the desired microorganism can be migrated at a favorably high recovery rate by setting the sweeping application rate at substantially 100 $\mu$m/sec or less, since the migrating rate of the microorganism is 100 $\mu$m/sec or less in the microorganism concentration condensing device of the present invention.

In addition, the microorganism contained in the test liquid and subjected to condensation can be moved by electrophoresis when a voltage is applied. For example, there are Colon bacilli, yellow staphylococci and the like.

Furthermore, as a material for constituting the electrodes, conventional materials can be used; aluminum foil, copper foil, a carbon mesh, a foamed metal, carbon fiber, a carbon mesh, and the like can be exemplified.

Moreover, as a material for constituting the substrate, insulating materials such as a glass plate, a glass mat, a polypropylene non-woven fabric and a polyester non-woven fabric, and the like can be used for example.

A microorganism concentration condensing device in accordance with a first electrochemical device of the present invention will be described below more specifically by using embodiments; however, the present invention is not limited to these embodiments.

Embodiment 1

Figure 3:
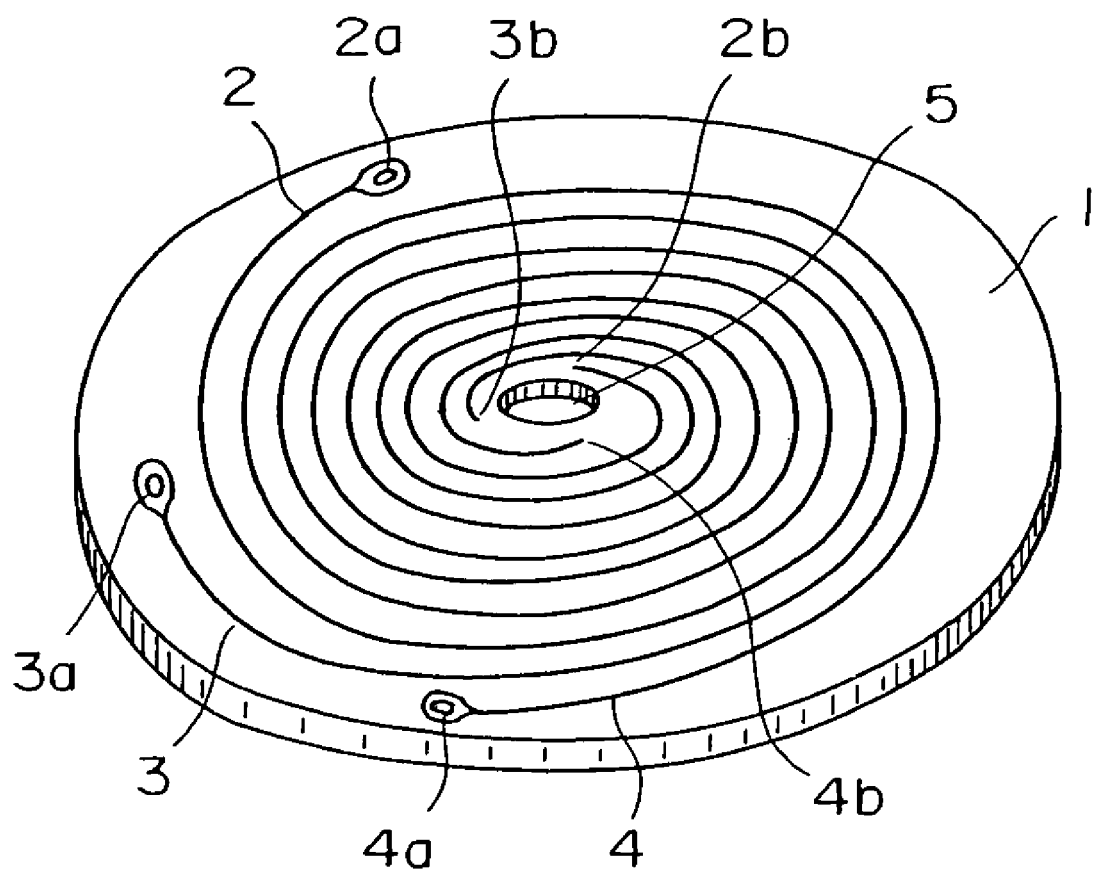
FIG. 3 is a schematic perspective view showing the structure of the main portion of a microorganism concentration condensing device comprising vortex-type electrodes in accordance with the present invention.

FIG. 3 is a schematic perspective view showing the structure of the main portion of a microorganism concentration condensing device comprising vortex-type electrodes in accordance with the present invention. Three electrodes are used herein. In this embodiment, the above-mentioned electrodes are vortex-type electrodes, and the above-mentioned substrate is a flat substrate. Furthermore, the above-mentioned electrodes are disposed on the above-mentioned flat substrate so that the electrodes extend to the same center from the outer end portions to the inner end portions thereof without overlapping each other.

As shown in FIG. 3, vortex-type electrodes 2, 3 and 4 are disposed on a substrate 1 made of an insulating material such as a glass plate. This substrate may be constituted by a porous material, through which a microorganism can pass. In addition, the substrate should only have a flat portion on which the vortex-type electrodes can be disposed, and the shape thereof may be circular or rectangular.

The electrodes are disposed so that they do not overlap each other from the outer end portions 2a, 3a and 4a to the inner end portions 2b, 3b and 4b of the electrodes. In other words, the electrodes are disposed to have a structure in which the end portions 2a, 3a and 4a of the electrodes, used as the electrode lead-out ports, are provided at the peripheral ends of the substrate 1, and the electrodes are disposed so that they do not make contact with each other. In addition, the electrodes extend to the same center (a microorganism exit 5, herein). The electrodes can be disposed three-dimensionally at positions opposed to each other, instead of being disposed on the same plane.

For example, two flat substrates provided with the above-mentioned vortex-type electrodes are disposed so that the vortex-type electrodes on the flat substrates are opposed to each other with a space therebetween, and the concentration of the microorganism concentration of a test liquid can be condensed in the space. In other words, the above-mentioned electrodes may form paired electrodes.

The operation principle of this microorganism concentration condensing device is described above; the microorganism can be moved from the outer peripheral portions of the vortex-type electrodes to the centers of the vortex-type electrodes by controlling the above-mentioned sweeping rate for applying a voltage to the respective electrodes in sequence. Consequently, only the microorganism in the test liquid can be moved to the microorganism exit 5; as a result, it is possible to obtain a test liquid having a condensed microorganism concentration.

By providing the microorganism exit 5 at the central portions of the vortex-type electrodes, it is possible to theoretically obtain a concentration rate equal to the ratio of the outer periphery and the inner periphery of the vortex-type electrode, that is, the ratio of the diameter of the outer periphery and the diameter of the inner periphery.

In addition, as the result of wholehearted studies, the inventors of the present invention have found that the microorganism concentration condensing device in accordance with the embodiment 1 should preferably be operated in the following conditions, for example.

Figure 4:
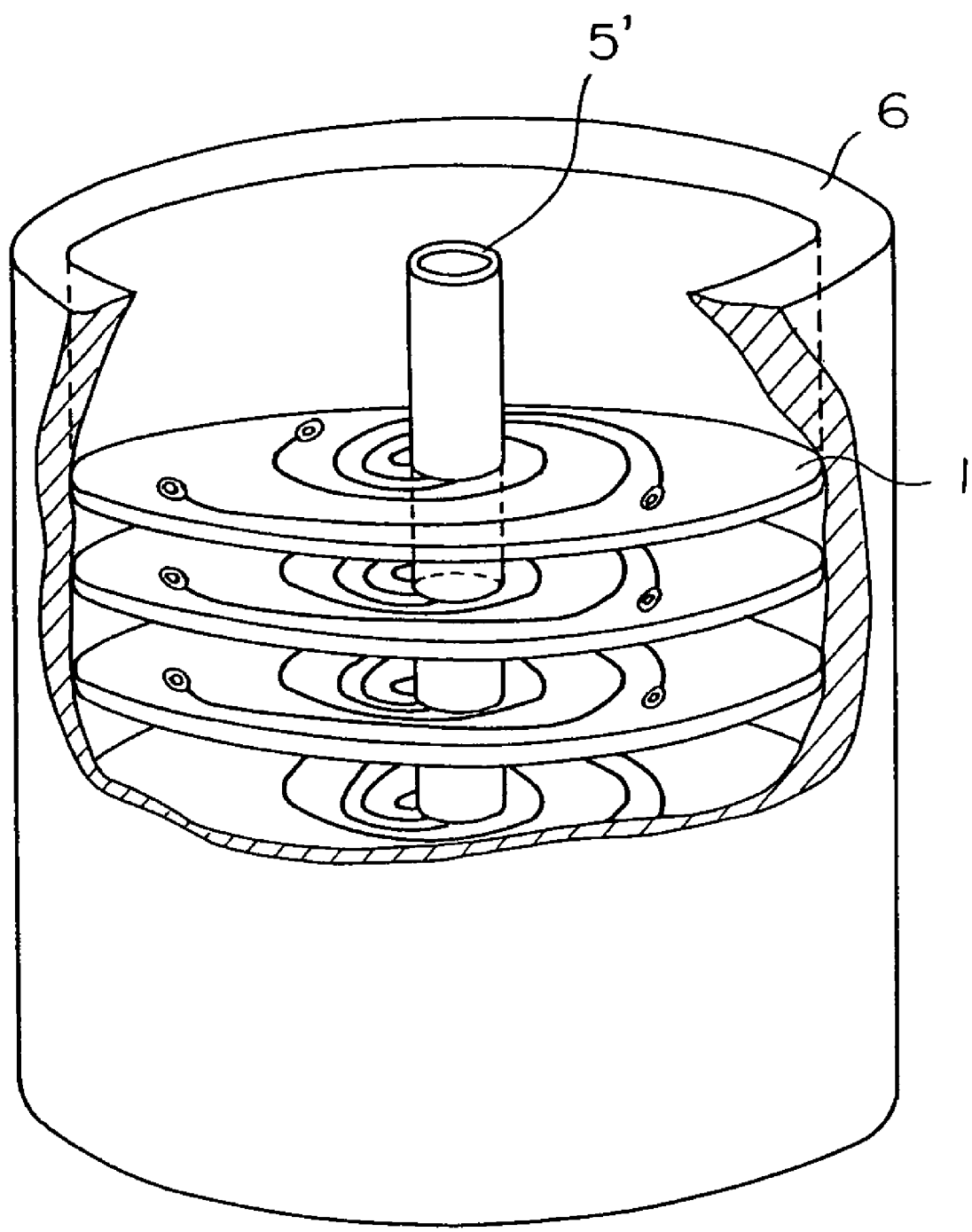
FIG. 4 is a partially cutaway schematic perspective view showing a microorganism concentration condensing device in accordance with the present invention, in which plural flat substrates having the vortex-type electrodes shown in FIG. 3 are stacked.
Figure 5:
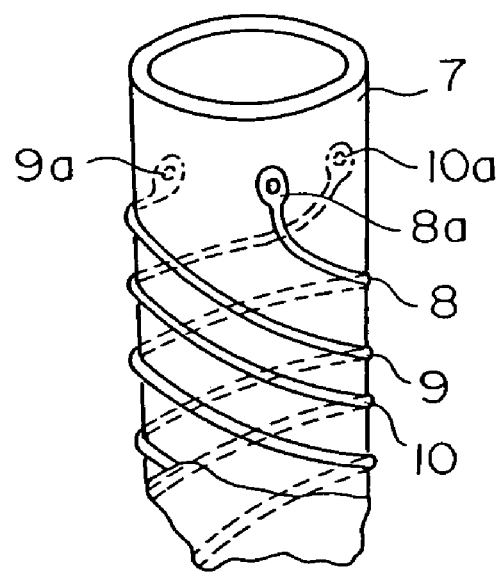
FIG. 5 is a schematic perspective view showing the structure of the main portion of a microorganism concentration condensing device comprising spiral electrodes in accordance with the present invention.
Figure 6:
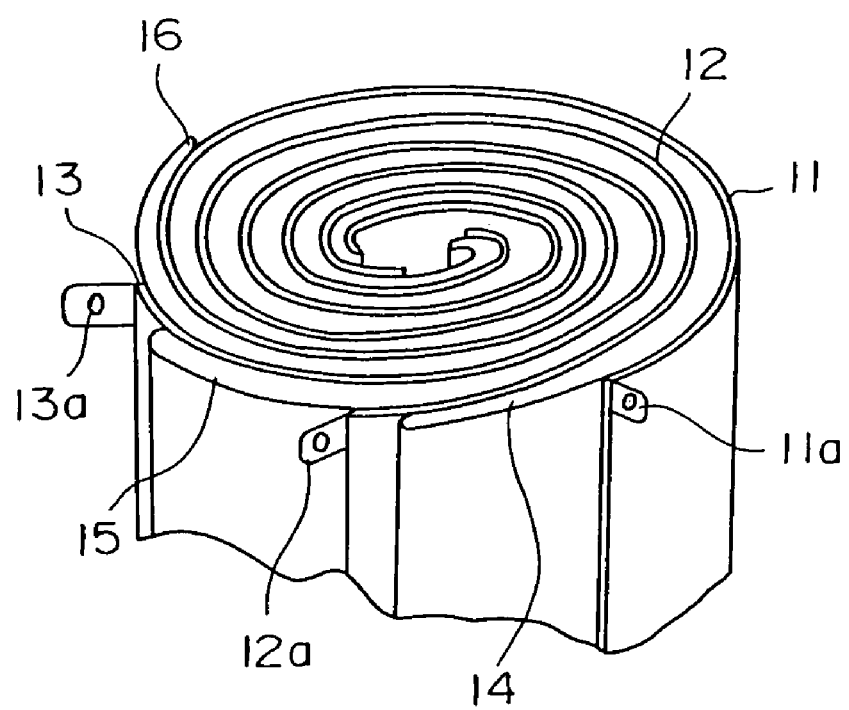
FIG. 6 is a schematic perspective view showing the structure of the main portion of a microorganism concentration condensing device comprising sheet-shaped porous electrodes in accordance with the present invention.

Applied voltage: 0.7 V (between electrodes)
Distance between electrodes: 86 $\mu$m (maximum 100 $\mu$m)
Bacteria movement distance: 20 $\mu$m/sec
Bacteria movement direction: to positive electrode (at the time of voltage application)
Electrode material: aluminum foil, copper foil
Substrate: glass plate To obtain a higher microorganism condensation effect, it is also possible to employ a devise an embodiment shown in FIG. 4. FIG. 4 is a partially cutaway schematic perspective view showing a microorganism concentration condensing device in accordance with the present invention, in which plural flat substrates having the vortex-type electrodes shown in FIG. 3 are stacked.

In the embodiment shown in FIG. 4, the plural flat substrates having the vortex-type electrodes shown in FIG. 3 are stacked, and a hollow core member 5' used as an electrode is provided at the microorganism exit 5 disposed at the center. The outer peripheries of the substrates are covered with a cylindrical member 6. In addition, by providing a groove or a through hole (not shown) in the hollow core member 5', the microorganism moved by electrophoresis may be recovered in a container (not shown) provided below the core member 5', for example.

Furthermore, in order to introduce a test liquid, a test liquid introduction portion may be constituted by disposing sheath-shaped member on the outside of the cylindrical member 6 and by providing a through hole or the like in the cylindrical member 6 communicating with the interior thereof, for example. A test liquid introduction device may be provided separately from the cylindrical member 6.

In this case, the hollow core member 5' in which the microorganism gathers should be positively charged, and the cylindrical member 6 should be negatively charged.

In accordance with this kind of embodiment, in the above-mentioned microorganism concentration measurement system, the effects of the microorganism concentration condensing device of the present invention can be enhanced further.

Embodiment 2

FIG. 5 is a schematic perspective view showing the structure of the main portion of a microorganism concentration condensing device comprising spiral electrodes in accordance with the present invention. In the microorganism concentration condensing device in accordance with this embodiment, the electrodes are spiral electrodes, and the substrate is a pillar-shaped substrate; the electrodes are disposed on the side face of the pillar-shaped portion so that the electrodes do not overlap each other from the upper end portions to the lower end portions thereof.

As shown in FIG. 5, three spiral electrodes 8, 9 and 10 are disposed on the side face of a cylindrical substrate 7 from the upper end portions 8*a*, 9*a* and 10*a* to the lower end portions (not shown) of the electrodes without overlapping each other. Although the cylindrical substrate 7 is shown as the pillar-shaped substrate, it may be a prism-shaped substrate, for example. Furthermore, it may be hollow.

The material for constituting the substrate may be the same as that mentioned in the above embodiment 1. For example, the above substrate may be constituted by a porous material or may be hollow so that the microorganism can pass through the inside of the substrate.

The spiral electrodes can be disposed three-dimensionally on concentric circles, not on the same plane.

For example, two hollow cylinders having different diameters are used as substrates, and a spiral electrode is provided on the outside face of the cylindrical substrate A having a smaller diameter. Another spiral electrode is provided on the inside face of the cylindrical substrate B having a larger diameter. Furthermore, the cylindrical substrate A is provided inside the cylindrical substrate B, with a space formed between the two substrates; in this space, the condensation of the microorganism concentration in a test liquid can be performed. In this way, the above electrodes may form paired electrodes.

In this microorganism concentration condensing device, by appropriately controlling the above-mentioned sweeping rate for voltage application as described above, the microorganism can be moved along the spiral electrodes from one end to the other end of the pillar-shaped substrate.

Furthermore, by providing a bacteria test liquid introduction portion (not shown) at one end of the pillar-shaped substrate and by providing a microorganism exit (not shown) at the other end, it is possible to attain efficient microorganism condensation.

Moreover, concrete operation conditions may be the same as those of the above-mentioned embodiment 1.

Embodiment 3

FIG. 6 is a schematic perspective view showing the structure of the main portion of a microorganism concentration condensing device comprising sheet-shaped porous electrodes in accordance with the present invention. In the microorganism concentration condensing device in accordance with this embodiment, the electrodes are sheet-shaped porous electrodes, and the substrates are sheet-shaped porous spacers. In addition, n ($n \geqq 3$) pieces of laminates, each comprising the above-mentioned electrode and spacer, are stacked in the order of electrode and spacer while the end portions of the electrodes in the laminates do not overlap each other; and the obtained laminates are wound.

Each of sheet-shaped porous electrodes 11, 12 and 13 has numerous pores through which the microorganism can transmit, and the electrodes are stacked and wound together with sheet-shaped porous spacers 14, 15 and 16, each of which is provided between the electrodes and through which the microorganism can transmit. In other words, the electrodes 11, 12 and 13 do not contact with each other, and each of electrode lead-out ports 11*a*, 12*a* and 13*a* is provided at one end of the periphery of each electrode.

The operation principle of the microorganism concentration condensing device in accordance with the present embodiment is as described above; by appropriately controlling the above-mentioned sweeping rate for voltage application to the electrodes, the microorganism can be moved from the outer peripheries to the center portions of the sheet-shaped electrodes appeared in vortex.

In this case, by providing a cylindrical member (not shown) used as a microorganism exit at the central portion of the vortex, for example, a condensation rate equal to the ratio of the outer periphery and the inner periphery of the vortex, that is, the ratio of the diameter of the outer periphery and the diameter of the inner periphery, can be obtained theoretically.

As a material for the sheet-shaped porous electrode used as the electrode in this case, a copper mesh, a foamed metal, a carbon mesh and the like can be exemplified. Furthermore, as a material for the sheet-shaped porous spacer used as the substrate, a polypropylene non-woven fabric and a polyester non-woven fabric can be exemplified.

Embodiment 4

It is also possible to obtain a microorganism concentration condensing device by forming a plurality of the substrates provided with the electrodes as described in the above-mentioned embodiment 3, connecting the lead-out portions 11$a$, 12$a$ and 13$a$ disposed at the respective electrodes, and connecting the plural substrates provided with the electrodes.

By using this kind of structure, it is possible to increase the amount of a test liquid for treatment, and the microorganism concentration condensing effect for the bacteria test liquid can be enhanced further.

By the microorganism concentration condensing device of the present invention, the condensation of the microorganism concentration in a test liquid can be carried out by using fewer process steps, more easily, in a shorter time, at higher quantitative and more stably, in comparison with a method in which the condensation of the microorganism concentration is carried out by filtering and re-extracting the test liquid containing the microorganism.

Further, in the microorganism concentration condensing device of the present invention, by appropriately selecting the materials for the components thereof, the device can be converted into a disposable type or a continuous-use type, and therefore has a wide range of applications.

Furthermore, the device can also be used as a bacteria removing device for water-purification pipes, food industry and the like, for example, as another effect thereof.

(ii) Bacteria Removing Device

Next, the present invention also provides a bacteria removing device comprising an inflow port for allowing a test liquid containing a microorganism to flow into the device, an inflow guide for guiding the test liquid from the above-mentioned inflow port to the vicinity of a positive electrode, at least n (n≧3) pieces of electrodes contacting with the test liquid flowed in and having a pore through which the test liquid passes, a negative electrode disposed to sandwich the n pieces of electrodes with respect to the positive electrode, a discharge port for discharging the test liquid having passed through the n pieces of electrodes, an outflow guide for guiding the flow of the test liquid to be discharged, and a circuit for sweepingly applying a voltage in a range such that it does not cause the electrolysis of the test liquid to the n pieces of electrodes sequentially in a constant direction.

In this bacteria removing device, a vortex-type electrode, which is obtained by winding n pieces of electrodes and n pieces of mesh-like electrodes while an insulating layer having pores through which the test liquid pass being held between the electrodes. It is effective that the direction of voltage application to the electrodes is perpendicular to the direction of the flow of the test liquid containing a microorganism.

Furthermore, it is effective that the n pieces of electrodes are porous flat electrodes having pores through which the test liquid can pass, that a structural body obtained by stacking the units several times, which is obtained by stacking an insulating layer having pores through which the test liquid can pass between the electrodes so as to be held therebetween, and that the direction of voltage application to the electrodes is set perpendicular or opposite to the flow direction of the bacteria liquid to be treated containing a microorganism.

Furthermore, it is effective that the circuit carries out the sweeping voltage application by: applying a negative voltage to the first electrode of the n pieces of electrodes, a positive voltage to the second electrode, and maintaining the electrodes other than the first and second electrodes in a no-connection state with voltage applied; in the next timing, applying a negative voltage to the second electrode, a positive voltage to the third electrode, and maintaining the electrodes other than the second and third electrodes in a no-connection state with no voltage applied; further in the next timing, by shifting the voltage application state one by one sequentially in the same manner as described above.

Furthermore, as the sweeping voltage application timing of the above-mentioned circuit, it is effective that the time for the change from the negative voltage application to the positive voltage application is 100 $\mu$m/sec or less by converting into the time of the distance between electrodes/sweeping timing (1 cycle time/n).

Furthermore, a plurality of the above-mentioned electrode structures may be disposed.

Embodiment 5

Figure 7:
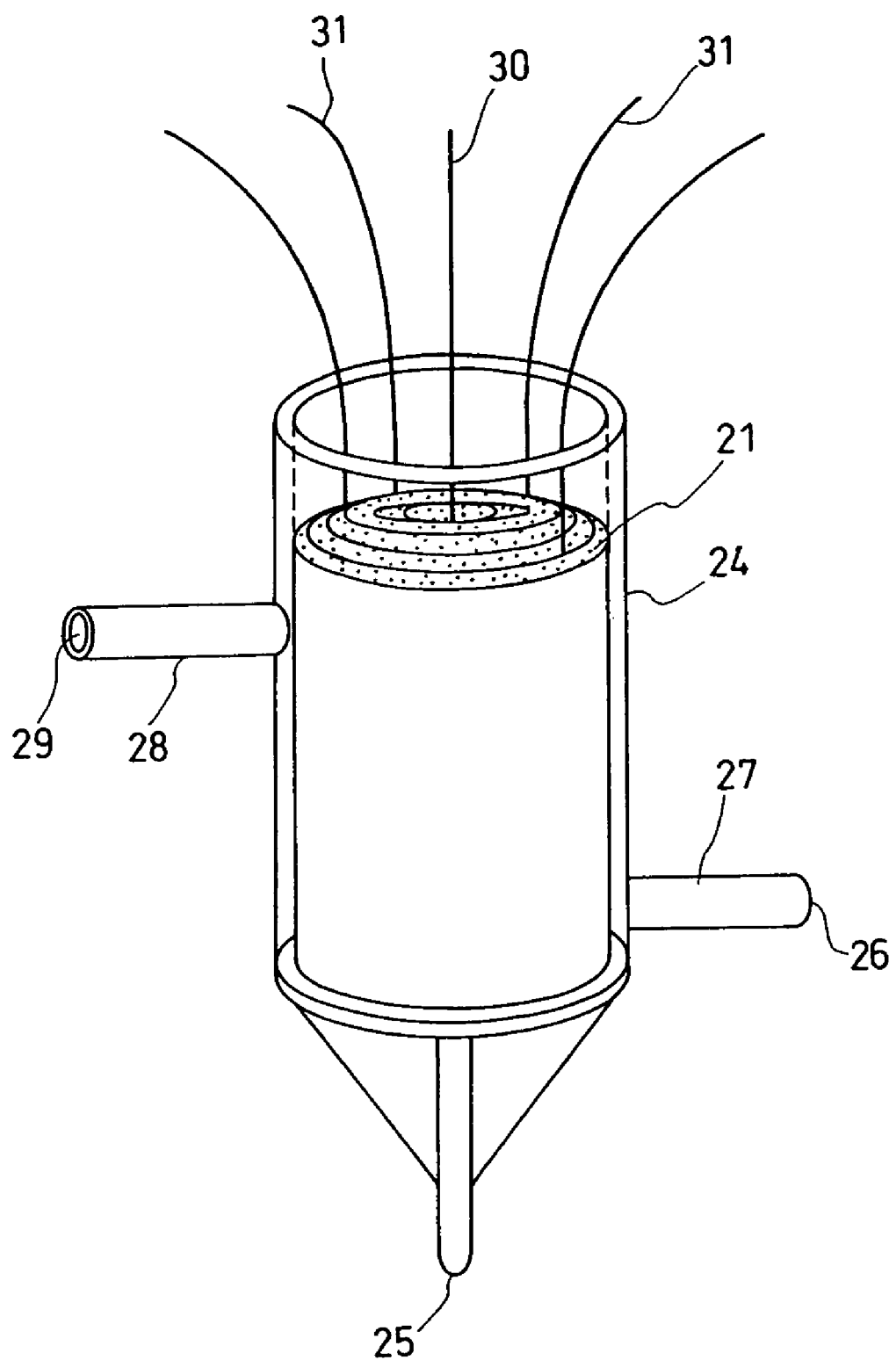
FIG. 7 is a schematic view showing the structure of a bacteria removing device comprising a wound type electrode in accordance with the present invention.
Figure 8:
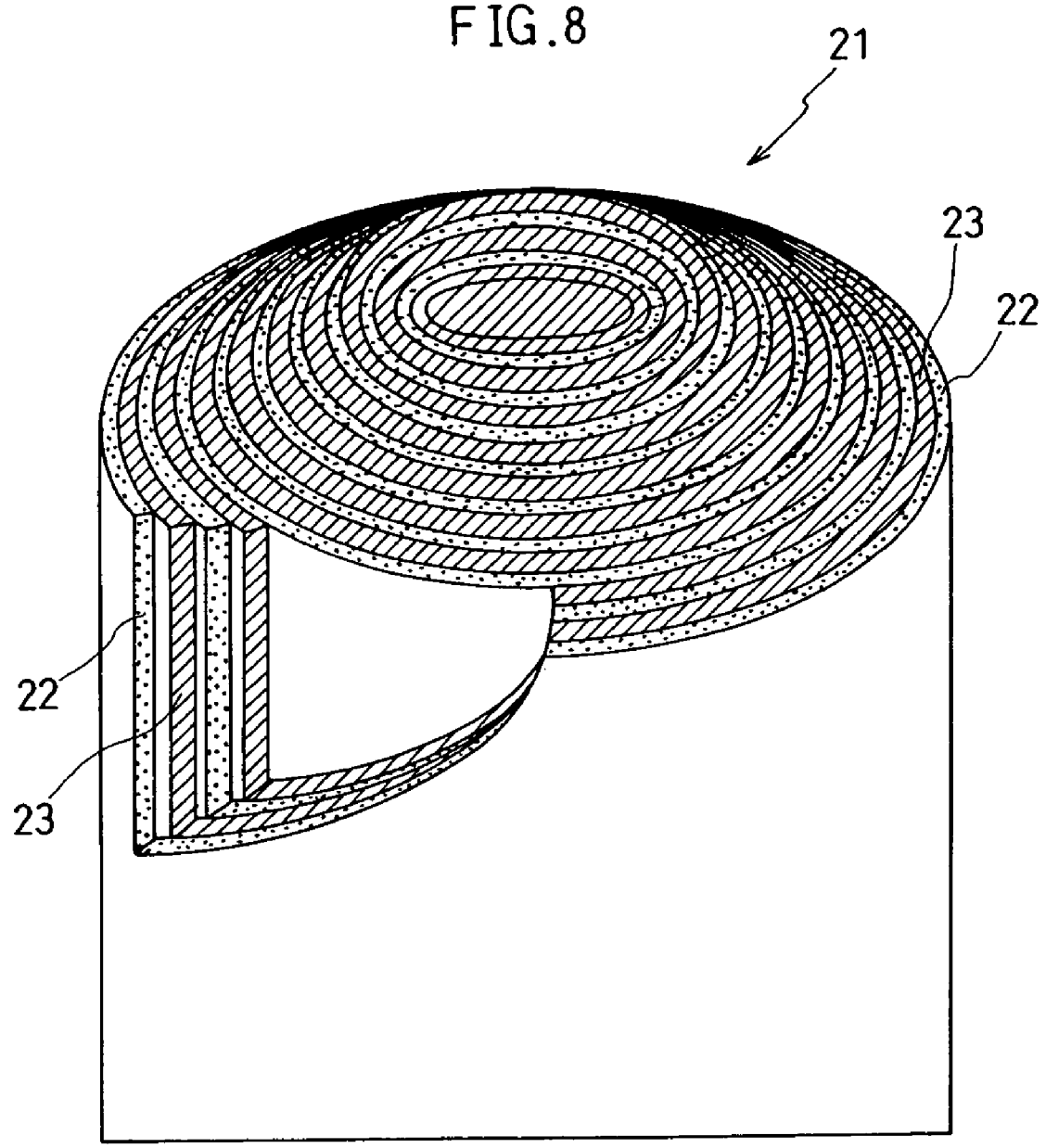
FIG. 8 is a partially cutaway schematic perspective view showing the wound type electrode of the bacteria removing device shown in FIG. 7.

In a bacteria removing device having a wound type electrode in accordance with the first electrochemical device of the present invention, a schematic view showing the structure of a bacteria removing device in which the number of the wound type electrodes is three is given in FIG. 7. Furthermore, a partially cutaway schematic perspective view showing the wound type electrode 21 of the bacteria removing device shown in FIG. 7 is given in FIG. 8.

First, a method of producing the bacteria removing device in accordance with the present invention will be described. A 30-mesh copper mesh formed of copper wires having a diameter of 0.22 mm was cut to a size of 10 mm in width and 30 cm in length, an end portion was treated, and a process for taking out a lead wire from the end portion was carried out so as to make three mesh-like electrodes 22.

Next, three mesh-like insulating layers 23, each formed of a 30-mesh polyester mesh having a thickness of about 300 $\mu$m and a size larger than the above-mentioned copper mesh by 1 cm in width and length were made.

By alternately stacking the above-mentioned copper meshes and insulating layers and by winding them around a core member (not shown) of about 5 mm, a wound structure having a diameter of about 4 cm was obtained. The same polyester mesh as that used for the insulating layer was wound around the surface of this wound structure, and the same copper mesh as that used for the above-mentioned electrode was wound around the surface of the wound structure, whereby the wound type electrode 21 was obtained. This copper mesh was subjected to the same lead taking out process as that for the above-mentioned electrode.

This wound type electrode 21 is accommodated in a cylindrical container 24 for the bacteria removing device having an inside diameter of about 4.5 cm. This container 24 has a size capable of snugly accommodating the above-mentioned wound type electrode. The bottom portion has a flat structure, the central portion is provided with a washing-out port 25, and the bottom side face is provided with a treated test liquid discharge port 26. In addition, the bottom portion is provided with a funnel-shaped outflow guide 27 so that the test liquid can be discharged without causing turbulence.

The above-mentioned wound type electrode was disposed on the outflow guide 27 so as to be mounted thereon, and a funnel-shaped inflow guide 28 was provided thereon to smoothen the introduction of the test liquid. A test liquid inflow port 29 was provided on the side face of the inflow guide 28, thereby obtaining a structure not allowing the test liquid to leak at the inflow port and the lower portions.

After the above-mentioned structure was completed, the core member was extracted, and a copper wire 30 having a diameter of about 0.5 mm was inserted into the space portion for the core member so as to pass through down to the washing-out port 25. Lead wires 31 were taken out from the upper portion of the container 24 together with the copper wire 30 while the lead wires were covered with sleeves to prevent electrical contact among them. This completes the main portion of the bacteria removing device.

Next, a circuit for driving the main unit portion of the bacteria removing device completed as described above and the operation principle will be described.

The circuit used to drive this bacteria removing device may be a relay circuit or a semiconductor circuit, and sequentially repeats a time for connection to the positive electrode of a power source generating a voltage of 0.7 V, a time for connection to the negative electrode thereof and a time for no connection to the power source circuit in sequence.

The bacteria removing device performs bacteria removal in a period from the entry of the test liquid into the test liquid inflow port to the discharge from the test liquid discharge port. Namely, the bacteria removing device comprises at least n (n≧3) pieces of electrodes contacting with the test liquid, a pair of electrodes comprising a positive electrode at the outermost shell and a negative electrode at the central portion, disposed to sandwich these n pieces of electrodes, and a circuit for sweepingly applying a voltage in a range such that it does not cause the electrolysis of the above-mentioned test liquid to the above-mentioned electrodes sequentially in a constant direction, in which the microorganism in the test liquid can be transferred to the central portion, and the microorganism can be discharged from the washing-out port.

This bacteria removing device induces the microorganism in the test liquid to the stacked electrodes and sweepingly applies the voltage to the electrodes to move the microorganism from the vicinity of one electrode and collect in the vicinity of the other electrode, thereby discharges the microorganism after restricting the movement of the microorganism finally. In the meantime, the test liquid containing the microorganism supplied to the present device is microorganism-removed.

A structure having three wound electrodes was taken as an example of the structure of the present invention; however, the quantity is not limited in particular if it is three or more. The case wherein the number of the wound electrodes is three is taken as an example of the structure and explained as a representative structure.

First, a voltage in a range such that it does not cause the electrolysis of the test liquid is applied to the electrodes disposed in accordance with the above-mentioned structure. The voltage in a range such that it does not cause the electrolysis of the test liquid is determined depending on the kind and amount of the electrode and the solvent or electrolyte contained in the test liquid. In the case of water used for ordinary life and not containing any special salt components, the voltage may be 1 V or less. In the present embodiment, 0.7 V was used.

By applying such a voltage, it is possible to transfer the negatively charged microorganism to the positive electrode side by electrophoresis, without deteriorating the test liquid by electrolysis. In other words, by using one of the electrodes as a negative electrode and by using the other as a positive electrode, it is possible to immigrate the microorganism from the negative portion to the positive portion. By sweeping this voltage application from the outer peripheral side to the inner peripheral side of the container for the bacteria removing device, the concentration of the microorganism in the vicinity of the electrode on the outer peripheral side in the container can be decreased. By continuously carrying out this operation and by continuously taking out the treated liquid on the outer peripheral side, a test liquid having lower microorganism concentration can be obtained.

In addition, the closer to the vicinity of the electrode on the inner peripheral side, the higher the concentration of the microorganism in the test liquid, whereby a large quantity of the microorganism is condensed at the electrode on the innermost side. While the microorganism is moved several times repeatedly, their activity is lowered. As a result, the condensed microorganisms become present close to each other, and their splitting-growing characteristics are also lowered. Since the washing-out port 25 is provided at the innermost electrode, the above collected microorganisms are discharged continuously.

The method of applying a voltage to each electrode will be described below in more detail.

The application of the voltage is preferably carried out sequentially at constant intervals in order to allow the microorganism to migrate along the electrodes in a constant direction. It is therefore preferable to apply a pulse-shaped potential.

TABLE 1 indicates the movement of the microorganism in the test liquid depending on the voltage application state and timing for a part of the electrodes arranged in the bacteria removing device having the wound type electrode in accordance with the present embodiment.

The electrodes are designated as a first electrode, a second electrode and a third electrode respectively in the migration direction of the microorganism; a voltage is applied to the first electrode, the second electrode and the third electrode in this order; after this, the voltage is applied again to the first electrode (designated as a fourth electrode in the table), and to the second electrode and the third electrode in sequence, and this sequence is repeated.

TABLE 1

| Electrode | Polarity of applied voltage - microorganism migration direction | | | |
|---|---|---|---|---|
| First electrode | − ↓ | NC • | + • | − ↓ |
| Second electrode | + • | − ↓ | NC • | + • |
| Third electrode | NC • | + • | − ↓ | NC • |
| Fourth electrode | − ↓ | NC • | + • | − ↓ |

More specifically, a negative voltage is applied to the first electrode, a positive voltage is applied to the second electrode, and the third electrode is not connected to the power source. In this case, the microorganism is induced to the positive voltage application side and move from the first electrode to the second electrode. Since the negative voltage is applied to the fourth electrode, i.e., the first electrode in the next cycle, and the third electrode is not connected, an induction phenomenon occurs between the second electrode and the fourth electrode and, however, the movement due to the induction occurs very rarely because the electrodes are apart from each other. Consequently, at this timing, the microorganism present between the first electrode and the second electrode move from the first electrode to the second electrode.

At the next timing, the first electrode is not connected to the power source, and the second electrode is connected to the negative electrode, and the third electrode is connected to the positive electrode. As a result, the fourth electrode, i.e., the first electrode in the next cycle, is not connected. On the basis of the above-mentioned principle, the microorganism present between the second electrode and the third electrode move from the second electrode to the third electrode.

At the further next timing, the first electrode is connected to the positive electrode, the second electrode is not connected to the power source, the third electrode is connected to the negative electrode, and the fourth electrode, i.e., the first electrode in the next cycle, is connected to the positive electrode. In this case, on the basis of the same principle as that described above, the microorganism present between the third electrode and the fourth electrode move to the fourth electrode.

With these considered comprehensively, the microorganism moves from the first electrode to the fourth electrode by carrying out the sweeping at the above-mentioned three timing operations sequentially. By continuing the sweep sequentially, the microorganism moves sequentially from the outermost electrode to the innermost electrode. This operation is carried out inside the container of the bacteria removing device, and a test liquid is supplied to the vicinity of the outermost shell, whereby the microorganism in the liquid is removed.

The voltage application is preferably carried out sequentially at constant intervals in order to allow the microorganism to migrate along the electrodes in a constant direction. For this reason, it is preferable to apply a pulse-shaped potential.

The duration of time between voltage application to one electrode and voltage application to the next electrode, i.e., the sweeping rate, differs depending on the distance between the electrodes, the thickness of the electrodes, the flow rate of the bacteria test liquid to be treated, environmental conditions such as the temperature of the liquid to be treated and the concentration of the electrolyte and the like; however, the rate is required to be substantially less than the rate of the microorganism migrating in the direction of the electrode to which an electric field is applied. As a result of experiments, the inventors of the present invention have found that the bacteria removal efficiency of the bacteria liquid in the treatment device can be enhanced by setting the application sweeping rate at substantially 100 $\mu$m/sec or less to collect and discharge the desired microorganism in the constant electrode direction, since the speed of the migrating microorganism is 100 $\mu$m/sec or less in the microorganism concentration condensing device of the present invention.

In addition, the microorganism subjected to bacteria removal can be moved by electrophoresis when a voltage is applied. Colon bacilli, yellow staphylococci and the like are taken as examples.

Furthermore, as a material for constituting the electrode, conventional materials can be used; aluminum foil, copper foil, a carbon mesh, a foamed metal, carbon fiber, a carbon mesh and the like can be exemplified.

Moreover, as a material for constituting the insulating layer, insulating materials such as glass wool, a polypropylene mesh, a polyester mesh or non-woven fabric thereof and the like can be exemplified.

In addition, as a result of earnest studies, the inventors of the present invention have found that the bacteria removing device in accordance with the embodiment 1 is preferably be operated in the following conditions, for example.

Applied voltage: 0.7 V (between electrodes)
Distance between electrodes: 200 $\mu$m
Bacteria movement distance: 20 $\mu$m/sec
Bacteria movement direction: to positive electrode (at the time of voltage application)
Electrode material: copper mesh (about 100 $\mu$m thickness)
Insulating layer: polyester mesh (about 200 $\mu$m thickness)

Embodiment 6

Figure 9:
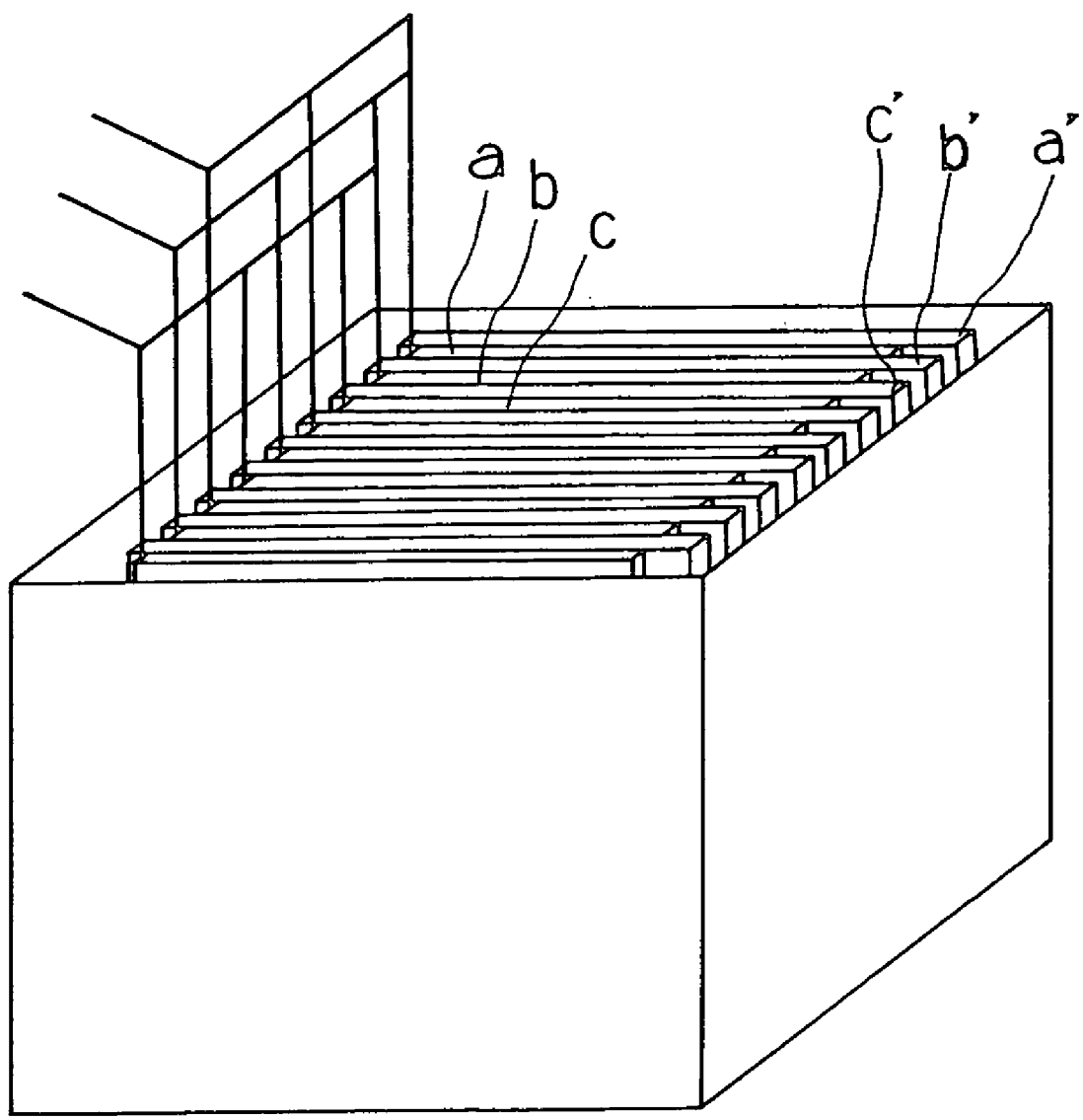
FIG. 9 is a schematic perspective view showing a box-shaped bacteria removing device in accordance with the present invention.

In the present embodiment, a bacteria removing device having a stack-type electrode was produced in order to form a box-shaped bacteria removing device. A schematic perspective view of a box-shaped bacteria removing device having three sets of stacked electrodes is shown in FIG. 9.

First, a method of producing the bacteria removing device in accordance with the present invention will be described. A 30-mesh copper mesh formed of copper wires having a diameter of 0.22 mm was cut to a size of 10 cm in width and 10 cm in length, and an end portion thereof was treated. Furthermore, a lead wire was taken out from the end portion, and 12 mesh electrodes (a, b and c) were prepared.

Next, 13 insulating layers (a', b' and c') each formed of a 30-mesh polyester mesh having a thickness of about 30 $\mu$m and larger than the above-mentioned copper mesh by 1 cm in width and length were prepared. In FIG. 9, the number of these layers is omitted.

First, one of the above-mentioned insulating layer is prepared, and at the center thereof, each of the above-mentioned copper meshes and insulating meshes are stacked alternately so that the copper meshes are insulated from each other; then, the last insulating layer is stacked. The lead-out portion of the first copper mesh is connected to the lead-out portion of the fourth copper mesh, and the lead-out portion of the seventh copper mesh is connected to the lead-out portion of the tenth copper mesh. In the same manner, the lead-out portion of the "n"th copper mesh is connected to the lead-out portion of the (n+3)th copper mesh, whereby three sets of electrodes comprising four connected copper meshes are formed.

These three sets of electrodes are accommodated in the box-shaped bacteria removing container, and an inflow guide plate is provided above the electrode on the side of the second copper such that no turbulence is occurred at the inflow port for a liquid to be treated and in the liquid. On the other hand, a discharge port for the liquid under treatment and a guide plate are provided below the inflow port for the liquid under treatment, thereby forming a bacteria removing device.

The timing of voltage application to the electrodes of this device and the operation principle thereof are the same as those of the embodiment 5.

Furthermore, as a material for the electrode, conventional materials can be used; aluminum foil, copper foil, a punching metal, a foamed metal, carbon fiber, a carbon mesh, a porous sintered metal and the like can be exemplified.

Moreover, as a material for the insulating layer, insulating materials allowing the microorganism to pass through, such as glass wool, a polypropylene mesh, a polyester mesh or non-woven fabrics thereof, porous ceramics and the like can be used for example.

In addition, as a result of earnest studies, the inventors of the present invention have found that the bacteria removing device in accordance with the embodiment 5 should preferably be operated in the following conditions, for example.

Applied voltage: 0.7 V (between electrodes)
Distance between electrodes: 200 $\mu$m
Bacteria movement distance: 20 $\mu$cm/sec
Bacteria movement direction: to positive electrode (at the time of voltage application)
Electrode material: copper mesh (about 100 $\mu$m thickness)
Insulating layer: polyester mesh (about 200 $\mu$m thickness)

The operation principle of the bacteria removing device in accordance with the present embodiment is described above; by appropriately controlling the above-mentioned sweeping rate for voltage application to the above-mentioned electrodes, microorganism can be moved from the outer peripheral portions of the sheet-shaped electrodes wound in the form of vortex to the central portion.

By producing a plurality of the containers provided with the electrodes described in the above-mentioned embodiments 5 and 6, and by connecting the lead-out portions provided for the respective electrodes to those corresponding thereto, it is possible to obtain a bacteria removing device in which plural containers provided with electrodes are connected.

By employing this kind of structure, it is possible to increase the amount of treatment, and it is possible to further enhance the microorganism removal effect for a bacteria liquid to be treated.

Due to the bacteria removing device of the present invention, it is possible to decrease the concentration of microorganism in a bacteria liquid to be treated by using fewer process steps, more easily, in a shorter time, more continuously and stably in comparison with a method for decreasing the concentration of microorganism by filtering the bacteria liquid to be treated containing a microorganism. Furthermore, the bacteria removing device of the present invention, by appropriately selecting the materials of the components, can be converted into a disposable type or a continuous-use type and has a wide range of applications. Furthermore, the device can be used as a bacteria removing device for water-purification pipes and food industry, and can also be used to remove a microorganism from circulation water system in living environment for example, as another effect thereof.

(iii) Electric Appliance provided with a Heat Exchanger

Furthermore, the present invention provides an electric appliance provided with a heat exchanger, comprising an electrode member opposed to the heat exchanger with a space therebetween and disposed in a condensed dew water discharged from the above heat exchanger at a position in which the electrode member is in contact with the above condensed dew water together with the surface of the above heat exchanger, and a voltage application means provided between the above heat exchanger and the above electrode member in order to move a microorganism present between the above heat exchanger and the above opposed member to the above electrode member direction.

In this case, it is effective that the voltage application means can apply a voltage in a range such that it does not cause the electrolysis of the condensed dew water.

In the above electric appliance, it is effective that the surface of the opposed member has a material capable of adsorbing and holding the microorganism, and it is also effective that the surface of the opposed member has a structure capable of adsorbing and holding the microorganism.

Furthermore, it is effective that the surface of the opposed member has a material capable of disinfecting the microorganism or capable of restricting the proliferation of microorganism, and it is effective that the surface of the opposed member has a structure capable of disinfecting the microorganisms or capable of restricting the proliferation of the microorganism. Furthermore, it is effective that the opposed member has an easily removable and cleanable structure.

Embodiment 7

Figure 10:
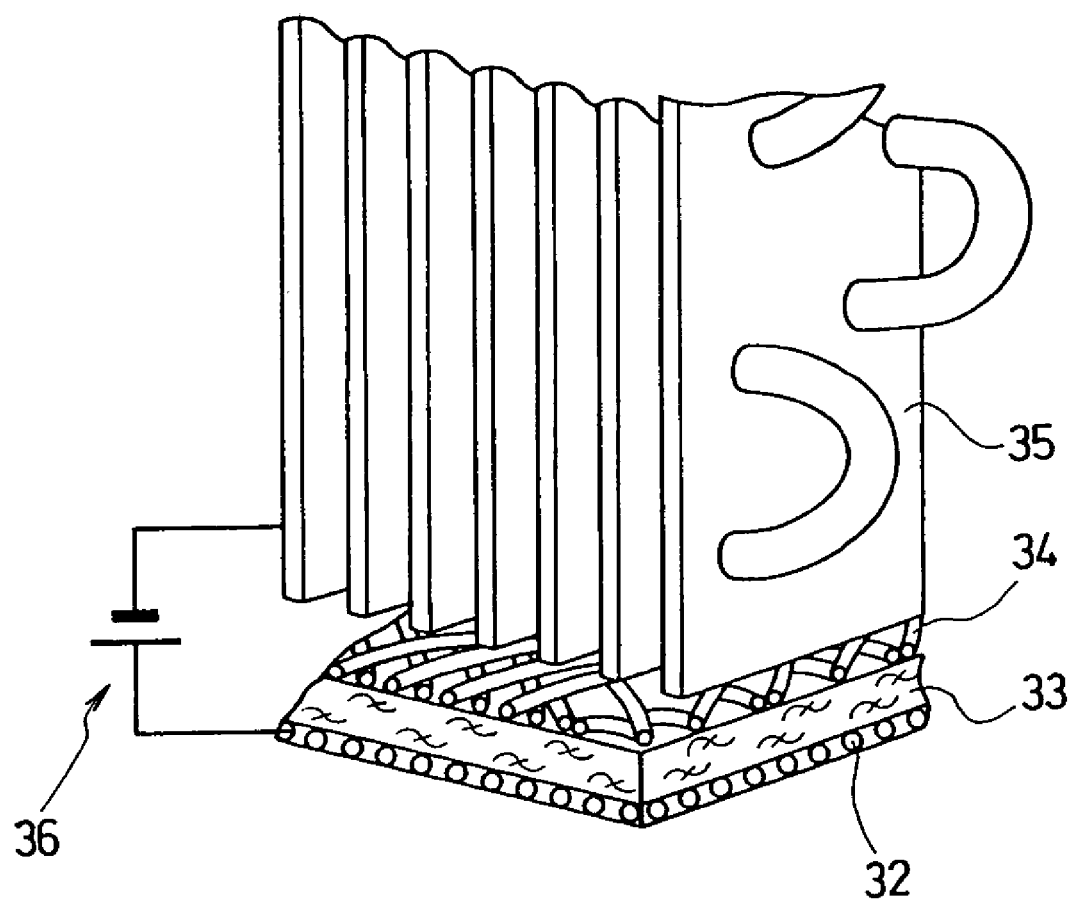
FIG. 10 is a schematic perspective view showing a heat exchanger portion in an air conditioner in accordance with the present invention.
Figure 11:
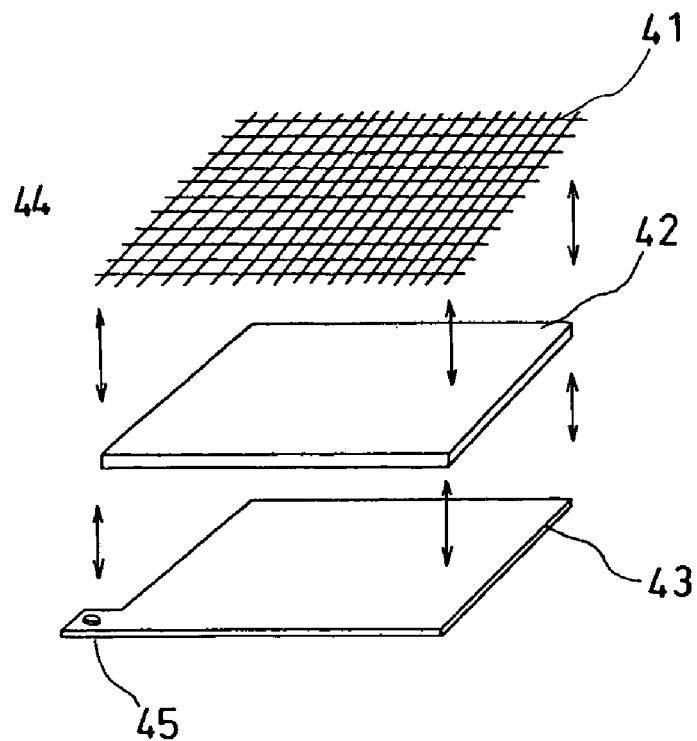
FIG. 11 is a schematic view showing the structure of a microorganism concentration condensing cell produced in accordance with embodiment 8 of the present invention.
Figure 12:
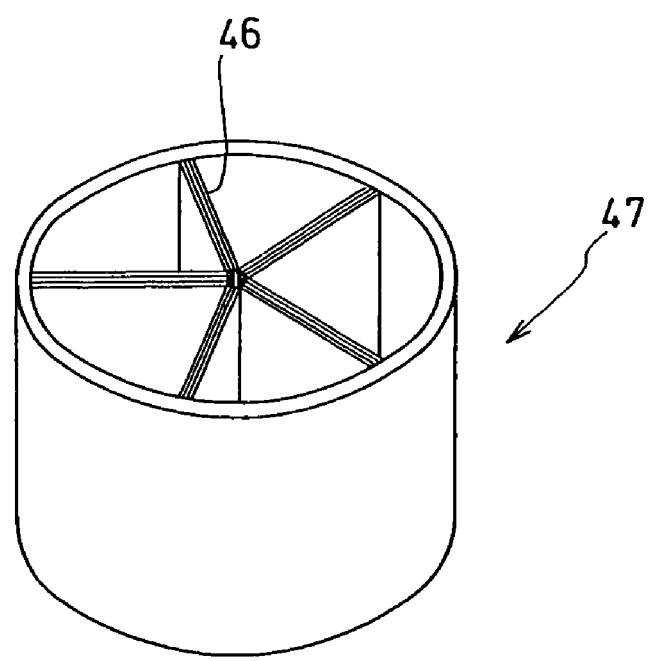
FIG. 12 is a schematic view showing the structure of a microorganism concentration condensing device produced in accordance with the embodiment 8 of the present invention.

FIG. 10 is a schematic perspective view showing a heat exchanger portion in an air conditioner in accordance with the present invention. An aluminum mesh 32 obtained by weaving aluminum wires of 50 $\mu$m into a mesh at an opening ratio of 50% and used as a metallic member, a hydrophilic non-woven fabric 33 of fibers comprising a hydrophilic and water-impermeable paper or the like, which is surface-treated with an antifungal agent or an antimicrobial agent such as thiabenzoimidazole (TBZ), a quaternary ammonium salt or a silver-based antimicrobial agent, and a polypropylene non-woven fabric 34 having a thickness of about 100 $\mu$m for securing the hydrophilic non-woven fabric 33 to the aluminum mesh 32 were stacked. This obtained laminate is disposed below the radiating aluminum fin 35 of the heat exchanger to which the condensed dew water of the heat exchanger flows down. A positive voltage of 0.7 V is applied to the aluminum mesh 32 with respect to the radiating fin 35 of the heat exchanger by a voltage application means 36.

In the air conditioner having the above-mentioned structure, at least one end thereof is in contact with a condensed dew water receiving pan (drain pan), and the condensed dew water in the drain pan is electrically connected to the level of the heating exchanger. The condensed dew water discharged from the drain pan is drained to prevent backflow, thereby electrically insulated from a catch basin used as a final discharge destination.

With this structure, the microorganism on the surface of the heat exchanger moves to the surface of the aluminum mesh 32 and is adsorbed by the hydrophilic non-woven fabric 33 on the surface of the aluminum mesh 32. At the same time, the proliferation of the microorganism is prevented by the antimicrobial and antifungal ingredients contained in the non-woven fabric 33.

In the above-mentioned air conditioner, the condensed dew water from which the microorganism is removed gathers in the drain pan, and is discharged to the catch basin. The movement of the microorganism from the surface of the heat exchanger (aluminum) to the surface of the metallic member (aluminum) is occurred; however, since the catch basin is insulated physically and electrically from the drain pan by water draining, the movement of the microorganism from the catch basin does not occur.

Furthermore, the air conditioning device having this structure is easily removable from the main unit of the air conditioner, and the hydrophilic non-woven fabric 33 therein is replaceable. When the effectiveness of the antimicrobial and antifungal agent applied to treat the hydrophilic non-woven fabric 33 is lowered and when the number of the microorganism adsorbed and held inside the non-woven fabric is increased, the effect can be restored by replacing the non-woven fabric 33 with a new one.

In the embodiment described above, the explanation with respect to an air conditioner is given; however, the embodiment can also be applied to electric appliances provided with heat exchangers such as car-mounted air conditioners, refrigerators, ice-making appliances, water-cooling appliances, cold reservoirs and vending machines.

In accordance with the electric appliance provided with the heat exchanger in accordance with the present invention, the cleanness of the surface of the heat exchanger containing a microorganism, which cannot be removed conventionally, can be enhanced and attained by electrochemical reactions. For this reason, the proliferation of microorganisms during the stop period of the electric appliance can be restricted, and the heat exchanger can be used as a part of infection prevention measures at hospitals and the like. The industrial value of the present invention is therefore great.

(2) With respect to Second Electrochemical Device (i) Microorganism Concentration Condensing Device and Microorganism Concentration Increasing Method Next, the present invention provides a microorganism concentration condensing device comprising a microorganism concentration condensing cell comprising two or more kinds of electrodes (metallic members) disposed opposite to each other with a space therebetween and having different oxidation/reduction potentials and a circuit (a short-circuit portion) for short-circuiting the above-mentioned electrodes, wherein a test liquid containing a microorganism is held in the above-mentioned space, and the microorganism is moved from an electrode having a higher oxidation/reduction potential to an electrode having a lower oxidation/reduction potential by short-circuiting the above-mentioned electrodes thereby to condense the concentration of the microorganism in the above-mentioned test liquid.

In the above-mentioned microorganism concentration condensing device, it is effective that the above cell has an introduction portion for the above test liquid at one end in the vicinity of the electrode having a higher oxidation/reduction potential, a discharge portion for the above test liquid at the other end, and a microorganism discharge portion and/or a microorganism adsorption portion in the vicinity of the electrode having a lower oxidation/reduction potential.

Furthermore, it is effective that an electrically insulating structural member through which the above test liquid can move is disposed in the above-mentioned space.

Furthermore, it is effective that the electrodes other than the electrode having the lowest oxidation/reduction potential have a structure capable of allowing the above test liquid to flow into the above space.

Furthermore, it is effective that the above-mentioned structure is a porous, mesh or brush structure.

Furthermore, it is effective that the electrodes other than the electrode having the lowest oxidation/reduction potential have the shape of a film through which a microorganism can pass, and that the electrode is stacked on the surface of an electrically insulating structural member through which the above test liquid can move.

Furthermore, a microorganism concentration condensing device having a plurality of the microorganism concentration condensing cells is also effective.

Furthermore, the present invention also provides a microorganism concentration condensing method comprising the steps of: disposing two or more kinds of electrodes having different oxidation/reduction potentials, opposite to each other with a space therebetween, (b) introducing a test liquid containing a microorganism in the above-mentioned space, (c) short-circuiting the above-mentioned electrodes, and (d) moving the microorganism from an electrode having a higher oxidation/reduction potential to an electrode having a lower oxidation/reduction potential by using the above-mentioned steps (b) and (c) to recover a condensed test liquid.

The inventors of the present invention have found that a microorganism can be allowed to migrate from a negative electrode to a positive electrode and the concentration of the microorganisms in the test liquid can be increased by forcibly applying a voltage across the electrodes in contact with the test liquid containing a microorganism. In other words, microorganisms such as colon bacilli and yellow staphylococci have charges on the surfaces and move depending on an electric field.

However, through experiments conducted earnestly by using electrodes made of various metals, the microorganism was able to be moved by using two kinds of electrodes and by simply short-circuiting the two electrodes, without forcibly applying a voltage across the electrodes.

Then, the inventors of the present invention have thus found that the different kinds of metallic members have different oxidation/reduction potentials (ionization tendencies), and have discovered that the microorganism moves from one metallic member to the other metallic member because of the above-mentioned difference in the oxidation/reduction potential. More specifically, the microorganism moves from a metallic member having a higher oxidation/reduction potential (having a lower ionization tendency) to a metallic member having a lower oxidation/reduction potential (having a higher ionization tendency).

In other words, the second electrochemical device in accordance with the present invention has been completed on the basis of the new findings regarding the oxidation/reduction potentials, obtained as the result of the above-mentioned examination.

The present invention relates to a microorganism concentration condensing device having a microorganism concentration condensing cell comprising two or more kinds of electrodes disposed opposite to each other with a space therebetween and having different oxidation/reduction potentials and a short-circuit portion for short-circuiting the above-mentioned electrodes, wherein the above-mentioned test liquid is held in the above space and a microorganism is moved from an electrode having a higher oxidation/reduction potential to an electrode having a lower oxidation/reduction potential by short-circuiting the above electrodes, thereby to condense the concentration of the microorganism in the above test liquid.

For convenience in understanding, the present invention will be explained below, while the above cell having two kinds of electrodes is taken as a typical example.

As the combination of the two kinds of electrodes, the combination may only contain electrodes having different oxidation/reduction potentials; however, in view of surely moving the microorganism in particular, it is preferable that the difference between the oxidation/reduction potentials is about 1.0 V.

Herein, in TABLE 2, some metallic members that can be used for the electrodes of the present invention and their oxidation/reduction potentials (standard electrode potentials E° in aqueous solution (25° C.)) were exemplified.

TABLE 2

| Kind of metal | Oxidation/reduction potential (V) |
|---|---|
| Au | +1.69 |
| Pt | +1.19 |
| Ag | +0.799 |
| Cu | +0.337 |
| Pb | −0.126 |
| Ni | −0.25 |
| Sb | −0.26 |
| Co | −0.277 |
| W | −0.32 |
| Fe | −0.440 |
| Sn | −0.50 |
| Cr | −0.744 |
| Zn | −0.763 |
| V | −1.23 |
| Al | −1.66 |
| Ti | −1.72 |
| Zr | −1.95 |
| Mg | −2.27 |

Among the metals listed in TABLE 2, it is preferable to use the combination of Au (+1.69 V) and Fe (−0.440 V) in considering that the difference between the oxidation/reduction potentials is large. Furthermore, in considering that they are inexpensive and easy to obtain, it is preferable to use the combination of Cu (+0.337 V) and Zn (−0.763 V).

The structure and form of this kind of metallic member are not limited in particular; a film form, a plate form, a bar form and the like through which the microorganism can pass are taken as examples. In addition, the metallic member may be a sintered metallic member, or a metallic member made by evaporation or sputtering.

However, in the present invention, since the microorganism is moved (allowed to migrate) from a metallic member having a higher oxidation/reduction potential to a metallic member having a lower oxidation/reduction potential, it is therefore preferable that an introduction portion and a discharge portion for a test liquid containing a microorganism are provided in the vicinity of the metallic member having the higher oxidation/reduction potential and that a microorganism discharge portion or a microorganism adsorption portion (described later) is provided in the vicinity of the metallic member having the lower oxidation/reduction potential.

In view of these, it is preferable that the metallic members other than the metallic member having the lowest oxidation/reduction potential have a structure wherein the above test liquid can flow into the above space. More specifically, the metallic member can have a porous structure such as a foamed metal, or a mesh or brush structure, for example.

Furthermore, the metallic members other than the metallic member having the lowest oxidation/reduction potential have the form of a film through which the microorganism can pass, and the metallic member may be stacked on the surface of an electrically insulating structural member through which the above test liquid can move.

The metallic members having low oxidation/reduction potentials may have this kind of structure and form as a matter of course.

Furthermore, it is preferable that an electrically insulating structural member through which the above-mentioned test liquid can move is disposed in the above space. This facilitates the capture of the microorganism contained in the test liquid in the above space, whereby the concentration of the microorganism can be condensed efficiently, and the scattering of the test liquid containing a microorganism to the outside can be prevented as much as possible.

As this kind of electrically insulating structural member, a non-woven fabric, a fabric, a continuous foam, paper and the like can be exemplified. In addition, as a material for constituting this structural member, thermoplastic resins such as polyester including polyethylene terephthalate and polypropylene can be exemplified.

Since this kind of electrically insulating structural member has captured the microorganism after use, it is made replaceable with a new one.

The above cell constituting the microorganism concentration condensing device of the present invention has a short-circuit portion for electrically short-circuiting two kinds of metallic members. By short-circuiting the above two kinds of metallic members, an electric field is generated between the metallic members having different oxidation/reduction potentials, whereby the microorganism can be moved.

This kind of short-circuit portion may be short-circuited in advance before the above test liquid is introduced, or can be short-circuited after the above test liquid is introduced.

It is preferable that the above short-circuit portion is constituted not to have a contact with the above test liquid so that the movement of the microorganism does not occur by the potential difference between the short-circuit portion and the above metallic members. For example, from the above metallic members, lead wires formed of the corresponding metals may be taken out and connected.

Furthermore, in the above cell, since the concentration of the microorganism in the test liquid containing a microorganism present in the vicinity of the metallic member having a higher oxidation/reduction potential is lowered, it is preferable to provide the above test liquid introduction portion for introducing (flowing) the above test liquid to one end in the vicinity of the metallic member, and that a discharge portion for discharging the test liquid having a lowered concentration of the microorganism is provided at the other end in the vicinity of the metallic member.

On the other hand, it is preferable to provide a discharge portion for discharging the above test liquid in which the microorganism is moved by the electric field and concentrated in the vicinity of the metallic member having a lower oxidation/reduction potential.

Furthermore, it is preferable to provide a microorganism adsorption portion in the vicinity of the metallic member having a lower oxidation/reduction potential. This adsorption portion can be formed by making the metallic member having a lower oxidation/reduction potential adsorbed onto silica gel or the like in layers.

As described above, although the case having two kinds of metallic members are used has been explained, even in the case having three or more kinds of metallic members are used, a microorganism condensation cell can also be produced by using a similar method.

For example, it is possible to have a structure in which a metallic member having the highest oxidation/reduction potential, an electrically insulating structural member, a metallic member having the second highest oxidation/reduction potential, an electrically insulating structural member, and a metallic member having the lowest oxidation/reduction potential are stacked in this order.

Furthermore, it is also possible to appropriately modify the arrangement of the metallic members to have a design such that the test liquid containing a microorganism is introduced from the vicinities of the plural metallic members and the test liquid after condensation is taken out from the vicinities of the other plural metallic members.

As describe above, the microorganism concentration condensing device of the present invention basically comprises the above microorganism concentration condensing cell.

For this reason, the microorganism concentration condensing device of the present invention may have a plurality of the above-mentioned microorganism concentration condensing cells. In this case, the plural cells may be connected mechanically to each other so that the short-circuit portion of each cell may be set on and off by a single switch. In addition, a single introduction portion may be formed by connecting the test liquid introduction portions of the respective cells. This is similarly applicable to the discharge portion for discharging the test liquid having a decreased concentration of the microorganism and to the test liquid discharge portion for discharging the test liquid having a condensed concentration of the microorganism.

The present invention also relates to a microorganism concentration condensing method based on the principle of the above microorganism concentration condensing device.

More specifically, the present invention relates to a microorganism concentration condensing method comprising the steps of: (a) disposing two or more kinds of metallic members having different oxidation/reduction potentials, opposite to each other with a space therebetween, (b) introducing a test liquid containing a microorganism in the above space, (c) short-circuiting the above metallic members, and (d) moving the microorganism from a metallic member having a higher oxidation/reduction potential to a metallic member having a lower oxidation/reduction potential by using the above steps (b) and (c) to recover the above test liquid after condensed.

These steps may be carried out in accordance with the explanation of the above-mentioned microorganism concentration condensing device of the present invention and, however, the sequence of step (a), step (b) and step (c) is not restricted in particular. For example, the two kinds of metallic members having a space therebetween and short-circuited beforehand may be immersed in the test liquid containing a microorganism, or the two kinds of metallic members having a space therebetween may be short-circuited after immersed in the test liquid containing a microorganism.

The present invention will be described below more specifically by using embodiments but is not limited thereto.

Embodiment 8

The present embodiment will be described referring to the drawings.

A gold mesh 41 woven by using a gold wire having a diameter of 50 $\mu$m and an opening ratio of 50%, a non-woven fabric spacer (electrically insulating structural member) 42 formed of polyethylene terephthalate and having a thickness of about 100 $\mu$m, and an iron foil sheet 43 having a thickness of 100 $\mu$m were stacked as shown in FIG. 11 thereby to form a microorganism concentration condensing cell (10 cm by 10 cm) 46.

Next, as shown in FIG. 12, after the cells, five in number, were disposed together so as to be arranged in star-like directions, one end of the gold mesh 41 was short-circuited to one end of the iron foil sheet 43 in each cell to form a short-circuit portion, thereby a microorganism concentration condensing device 47 in accordance with the present invention was obtained. The gold mesh 41 and the iron foil sheet 43 were provided with a terminal portion 44 or 45 for forming the short-circuit portion, respectively.

Next, the obtained microorganism concentration condensing device was gently immersed in a microorganism suspension (1 litter) containing about 1000 cfu/ml of colon bacilli as the microorganism. By this immersion, the above suspension flowed into the space in the non-woven spacer 42, and the microorganism moved toward the iron foil sheet 43 at a rate of about 2 $\mu$m/sec.

Embodiment 9

A microorganism concentration condensing cell and a microorganism concentration condensing device were produced in the same manner as that for the embodiment 8, except that a zinc foil sheet having a thickness of 100 $\mu$m and provided with silica gel on the surface was used as the microorganism adsorption layer, instead of the iron foil sheet 43.

When evaluated just as in the case of the embodiment 8, effects similar to those of the embodiment 1 were obtained.

Embodiment 10

A gold mesh woven by using a gold wire having a diameter of 50 $\mu$m and an opening ratio of 50%, a non-woven fabric spacer formed of polyethylene terephthalate and having a thickness of about 100 $\mu$m, an iron mesh woven by using an iron wire having a diameter of 100 $\mu$m and an opening ratio of 50%, and a zinc foil sheet having a thickness of 100 $\mu$m and provided with silica gel on the surface as the microorganism adsorption layer were stacked to form a microorganism concentration condensing cell. Next, by short-circuiting one end of the gold mesh to one end of the iron mesh, and one end of the iron mesh to one end of the zinc foil sheet, a microorganism concentration condensing device in accordance with the present invention was obtained.

Then, when evaluated just as in the case of the embodiment 8, effects similar to those of the embodiment 8 were obtained.

In accordance with the microorganism concentration condensing device of the present invention, the condensation of the microorganism in the above test liquid can be carried out by using fewer process steps, more easily, in a shorter time, at higher quantitative and more stably in comparison with a method in which the condensation of the concentration of the microorganisms is carried out by filtering and re-extracting the test liquid containing a microorganism.

Furthermore, when the device is used as a bacteria removing device, an effect of being capable of easily removing microorganisms is obtained without using an device such as an external power source.

(ii) Blood Component Induction Device and Blood Component Induction Method

Furthermore, the present invention provides a blood component induction device having a blood component induction cell comprising two or more kinds of electrodes disposed opposite to each other with a space therebetween and having different oxidation/reduction potentials and a circuit for short-circuiting the above electrodes, wherein a blood sample is held in the above space, and a blood cell component and/or a microorganism contained in the blood sample are moved from an electrode having a higher oxidation/reduction potential to an electrode having a lower oxidation/ reduction potential by short-circuiting the above electrodes, thereby to separate and remove the blood cell component and/or the microorganism from the above blood sample.

In this case, the test liquid containing particles covered with a protein corresponds to the blood sample containing a blood cell component and/or a microorganism.

In the above blood component induction device, it is effective that the above cell has an introduction portion for the above blood sample at one end in the vicinity of the electrode having a higher oxidation/reduction potential, a discharge portion or a holding portion for the above blood sample at the other end, and a discharge portion for discharging the microorganism contained in the blood sample and an adsorption portion for adsorbing the microorganism contained in the blood sample in the vicinity of the electrode having a lower oxidation/reduction potential, and/or has an adsorption portion for adsorbing the blood cell component contained in the blood sample.

Furthermore, it is effective that an electrically insulating structural member through which the blood component in the above blood sample can move is provided in the above space.

Furthermore, it is effective that the above electrode has the form of a mesh, a net, a film, a line or a brush.

Furthermore, it is effective that the electrodes other than the electrode having the lowest oxidation/reduction potential have a shape in which the above blood sample can flow into the above space. It is effective that the shape is a porous, mesh or brush.

Furthermore, it is effective that the electrodes other than the electrode having the lowest oxidation/reduction potential have the shape of a film through which the blood cell component and/or the microorganism contained in the blood sample can pass, and that the electrode is stacked on the surface of an electrically insulating structural member through which the above blood sample can move.

Furthermore, it is effective that a plurality of the above blood component induction cells are provided.

Furthermore, the present invention also provides a blood component induction method comprising the steps of: (a) disposing two or more kinds of electrodes having different oxidation/reduction potentials, opposite to each other with a space therebetween, (b) introducing a blood sample in the above-mentioned space, (c) short-circuiting the above-mentioned electrodes to move a blood cell component or a microorganism contained in the blood sample from an electrode having a higher oxidation/reduction potential to an electrode having a lower oxidation/reduction potential, and (d) recovering the blood sample from which the blood component are separated or the blood sample from which the microorganism are removed by using the step (c).

As described above, through experiments conducted earnestly by the inventors of the present invention by using electrodes made of various metals, the microorganism contained in the blood sample was able to be moved by using two electrodes made of different materials and by simply short-circuiting the two electrodes, without forcibly applying a voltage across the electrodes. In addition, not only the microorganism but also the blood cell component in the blood sample can be moved.

And the inventors of the present invention have discovered that the microorganism contained in the blood sample move from one metallic member to the other metallic member because the above different kinds of metallic members have different oxidation/reduction potentials (ionization tendencies). Furthermore, the inventors have also discovered that the blood cell component contained in the blood sample move from one metallic member to the other metallic member because of the difference between the above oxidation/reduction potentials.

More specifically, the microorganism and the blood cell component contained in the blood sample move from the metallic member having a higher oxidation/reduction potential (having a lower ionization tendency) to the metallic member having a lower oxidation/reduction potential (having a higher ionization tendency).

In other words, the blood component induction device in accordance with the present invention has been completed on the basis of the new findings regarding the oxidation/reduction potentials, obtained as the result of the above examination.

The present invention relates to a blood component induction device having a blood component induction cell comprising two or more kinds of metallic members disposed opposite to each other with a space therebetween and having different oxidation/reduction potentials and a short-circuit portion for short-circuiting the above-mentioned metallic members, wherein a blood sample is held in the above-mentioned space, and a blood cell component and/or a microorganism contained in the blood sample are moved from a metallic member having a higher oxidation/reduction potential to a metallic member having a lower oxidation/reduction potential by short-circuiting the above-mentioned metallic members, thereby to separate and remove the blood cell component and/or the microorganism from the above-mentioned blood sample.

"Blood sample" in the present invention is not only the blood itself but also a concept including blood diluted with isotonic sodium chloride solution, and liquid obtained by mixing component blood, pure water, an osmotic adjustment liquid, further water in living environment, waste water containing unwanted bacteria, a liquid containing a body fluid component, and the like, for example. Furthermore, it is also a concept widely including fluids in view of the fact that the blood sample may have some viscosity.

Furthermore, in accordance with the blood component induction device of the present invention, not only the blood cell component in a blood sample but also the microorganism, if contained, can be separated and removed. Consequently, the device can not only separate and remove the blood cell component or the microorganism but also separate and remove both simultaneously.

For convenience in understanding, the blood component induction device in accordance with the present invention will be explained below, while the above-mentioned cell including two kinds of metallic members is taken as a typical example.

The above-mentioned metallic members in accordance with the present invention function as the so-called electrodes. As the combination of the two kinds of metallic members, the combination of metallic members having different oxidation/reduction potentials may be used and, in view of securely moving the blood component and the microorganism contained in the blood sample in particular, it is preferable that the difference between the oxidation/reduction potentials is about 1.0 V.

Herein, some metallic members that can be used and their oxidation/reduction potentials (standard electrode potentials E° in aqueous solution (25° C.)) are shown in TABLE 2.

The structure and form of this kind of metallic member are not limited in particular and a mesh form, a film form, a line form, a brush form, a plate form, a bar form, a porous form and the like, through which the blood component or the microorganism contained in the blood sample can pass, are exemplified. In addition, the metallic member may be a sintered metallic member, or a metallic member made by plating, evaporation, CVD or sputtering.

Furthermore, in the case when a fiber-form metal is used, a mesh-form electrode or non-woven fabric-form electrode may be obtained by mixing natural fibers or synthetic fibers with metallic fibers.

However, in the present invention, since the blood cell component or the microorganism contained in the blood sample are moved (allowed to migrate) from a metallic member having a higher oxidation/reduction potential to a metallic member having a lower oxidation/reduction potential, it is therefore preferable that an introduction portion and a discharge portion for a blood sample are provided in the vicinity of the metallic member having the higher oxidation/reduction potential, and that a discharge portion or a adsorption portion for the blood component or the microorganism contained in the blood sample is provided in the vicinity of the metallic member having the lower oxidation/reduction potential.

In view of these, it is preferable that the metallic members other than the metallic member having the lowest oxidation/reduction potential have a form such that the above blood sample can flow into the above space. The metallic member can have a porous form, a mesh form or a brush form, for example. The metallic member may be a fabric, mesh or brush formed of thin metal wires or metal-treated fibers on the surface, for example. As described above, the metallic member may be formed by mixing and weaving natural fibers and synthetic fibers.

The metallic members having low oxidation/reduction potentials may have this kind of structure and form as a matter of course.

Furthermore, it is preferable that an electrically insulating structural member through which the blood component and the like in the above blood sample can move is disposed in the above space. This facilitates the capture of the test sample in the above space, thereby the removal of the blood cell component or the microorganism contained in the blood sample and the separation of the blood component can be performed efficiently, and the scattering of the blood sample to the outside can be prevented as much as possible.

As this kind of electrically insulating structural member, a non-woven fabric, a fabric, a continuous foam, paper and the like can be exemplified. In addition, as a material for constituting this structural member, cotton or thermoplastic resin such as polyester including polyethylene terephthalate or polypropylene can be exemplified.

Since this kind of electrically insulating structural member has captured the blood cell component or the microorganism contained in the blood sample after use, it is made replaceable with a new one.

In particular, in the case when the metallic members other than the metallic member having the lowest oxidation/reduction potential are formed into a film, through which the blood cell component or the microorganism contained in the blood sample can pass, it is preferable that the metallic member is stacked on the surface of the electrically insulating structural member through which the above blood sample can move.

The above-mentioned cell constituting the blood component induction device of the present invention has a short-circuit portion for electrically short-circuiting two kinds of metallic members. By short-circuiting the above two kinds of metallic members, an electric field is generated between the metallic members having different oxidation/reduction potentials, thereby the blood cell component and/or the microorganism contained in the blood sample can be moved.

Such a short-circuit portion may be short-circuited in advance before the blood sample is introduced, or may be short-circuited after the blood sample is introduced.

It is preferable that the above short-circuit portion is structured not to contact with the blood sample so that the blood cell component and/or the microorganism contained in the blood sample are not moved by the potential difference between the short-circuit portion and the above metallic members. For example, from the above-mentioned metallic members, lead wires formed of the corresponding metals may be taken out and connected.

Furthermore, in the above cell, since the concentration of the blood cell component and/or the microorganism contained in the blood sample present near the metallic member having a higher oxidation/reduction potential is lowered, it is preferable to provide an introduction portion for introducing (flowing) the blood sample to one end in the vicinity of the metallic member and to provide a discharge portion for discharging the blood sample having a decreased concentration of the blood cell component and/or the microorganism at the other end in the vicinity of the metallic member.

On the other hand, it is preferable that a discharge portion for discharging the blood sample in which the blood cell component and/or the microorganism contained in the blood sample are moved by the electric field and condensed is provided in the vicinity of the metallic member having a lower oxidation/reduction potential.

Furthermore, it is preferable that an adsorption portion for the blood cell component and/or the microorganism contained in the blood sample is provided in the vicinity of the metallic member having a lower oxidation/reduction potential. This adsorption portion can be formed by making the metallic member having a lower oxidation/reduction potential adsorb silica gel, polymer absorber or the like in layers. Moreover, a water absorbing layer for absorbing the blood sample may also be provided.

As described above, although the case having two kinds of metallic members are used has been explained, even in the case having three or more kinds of metallic members are used, an induction cell for the blood component contained in the blood sample can also be produced by using a similar method.

For example, it is possible to have a structure in which a metallic member having the highest oxidation/reduction potential, an electrically insulating structural member, a metallic member having the second highest oxidation/reduction potential, an electrically insulating structural member, . . . , an electrically insulating structural member, and a metallic member having the lowest oxidation/reduction potential are stacked in this order.

Furthermore, it is also possible to appropriately modify the arrangement of the metallic members to have a design in which the blood sample is introduced from the vicinities of the plural metallic members and the blood sample after the removal of bacteria or the separation of blood cell component is taken out from the vicinities of the other plural metallic members.

As describe above, the blood component induction device of the present invention is basically formed of the above blood component induction cell.

Therefore, the blood component induction device of the present invention may have a plurality of the above blood component induction cells. In this case, the plural cells may be connected mechanically to each other so that the short-circuit portion of each cell can be set on and off by a single switch. In addition, a single introduction portion may be formed by connecting the blood introduction portions of the respective cells. This is similarly applicable to the discharge portion for discharging the blood sample having a decreased concentration of the blood cell component or the microorganism and to the discharge portion for discharging the blood sample having an increased concentration of the blood cell component or the microorganism.

The present invention also relates to a blood component induction method based on the principle of the above-mentioned blood component induction device.

More specifically, the present invention relates to a blood component induction method comprising the steps of: (a) disposing two or more kinds of metallic members having different oxidation/reduction potentials, opposite to each other with a space therebetween, (b) introducing a blood sample in the above-mentioned space, (c) short-circuiting the above-mentioned metallic members, and (d) recovering the blood sample from which bacteria are removed by moving a blood cell component and/or a microorganism contained in the blood sample from a metallic member having a higher oxidation/reduction potential to a metallic member having a lower oxidation/reduction potential by using the above-mentioned steps (b) and (c).

These steps may be carried out in accordance with the explanation of the above-mentioned blood component induction device of the present invention but the sequence of step (a), step (b) and step (c) is not restricted in particular. For example, the two kinds of metallic members having a space therebetween and short-circuited beforehand may be immersed in the blood sample, or the two kinds of metallic members having a space therebetween may be short-circuited after immersed in the blood sample.

The blood component induction device in accordance with the present invention having the above-mentioned structure can be applied to for example first-aid adhesive tapes, sanitary napkins, medical adhesive tapes, sterilized gauze and sterilized sheets, and more specifically articles such as wound protection dressing, catheter fixing pads, hemostatic adhesive tapes, sterilized skin closures, sterilized ramie sheets, disposable surgical operation gowns and the like.

In the case when the device is applied to a first-aid adhesive tape in particular, it is effective to provide a disinfecting layer obtained by applying a disinfecting agent to the surface of a metallic member having a low oxidation/reduction potential in order to induce the microorganism to the vicinity of the metallic member having a low oxidation/reduction potential. Furthermore, in the case when the device is applied to a sanitary napkin, it is effective to provide a water-absorbing layer formed of water-absorbing resin in order to absorb moisture.

Furthermore, the shape and dimensions of the blood component induction device in accordance with the present invention are not limited in particular, but may be adjusted appropriately depending on the shape and dimensions of articles to be applied.

The blood component induction device in accordance with the present invention will be described below more specifically by using embodiments but is not limited thereto.

Embodiment 11

An example in which the blood component induction device in accordance with the present invention is applied to a first-aid adhesive tape will be described referring to a drawing.

Figure 13:
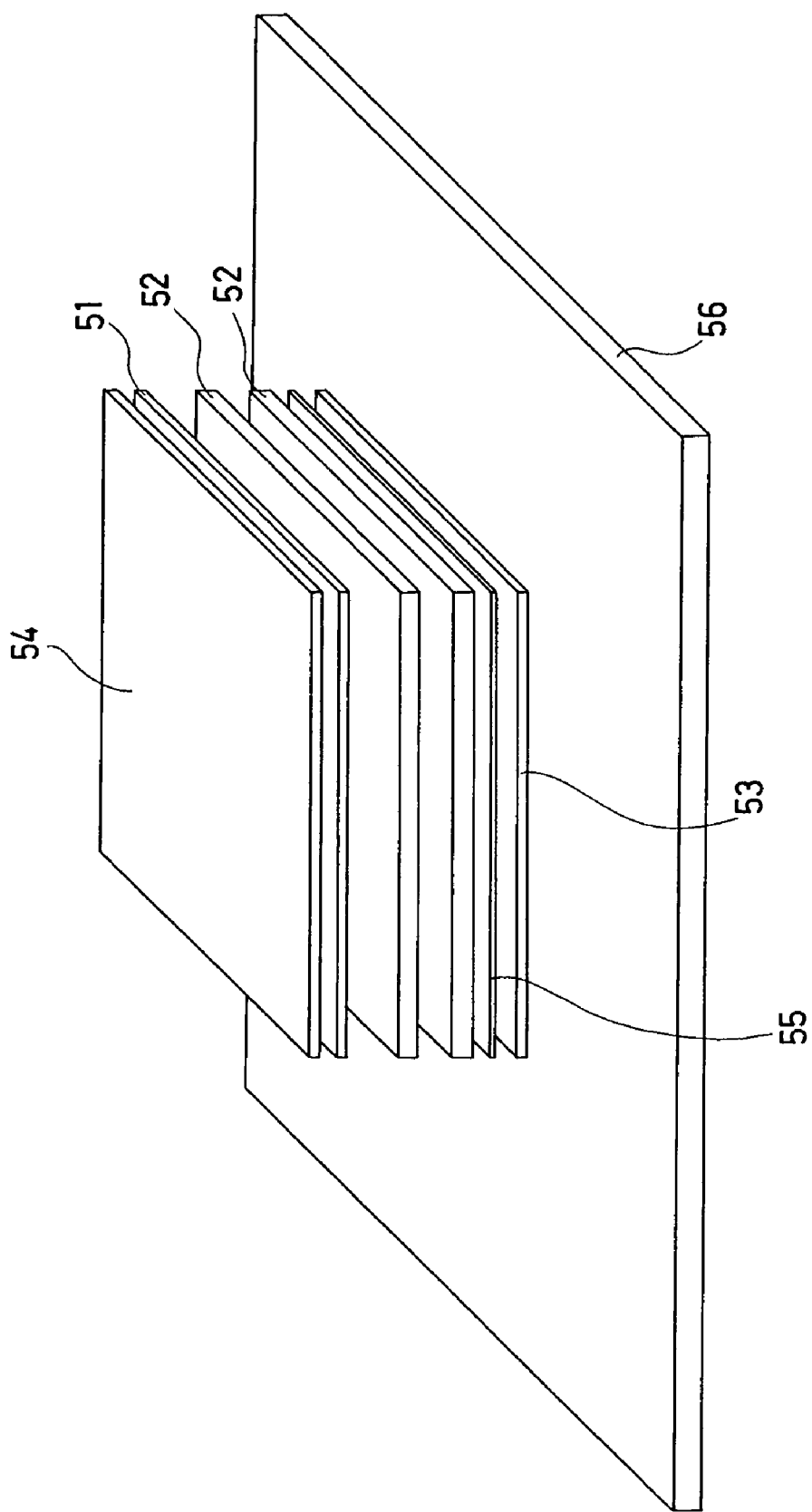
FIG. 13 is a view showing the structure of a first-aid adhesive tape in accordance with an embodiment of a blood component inducting device of the present invention.

FIG. 13 is a view showing the structure of a first-aid adhesive tape in accordance with an embodiment of the blood component induction device of the present invention. As shown in FIG. 13, in the first-aid adhesive tape in accordance with the present invention, a mesh-shaped electrode 51 (a metallic member having a higher oxidation/reduction potential) formed of a mixture of gold wires and synthetic fibers being hard to stick to tissue, each having a diameter of 10 $\mu$m, and spacers 52 (two sheets) obtained by processing fibers, which are hydrophilic and hard to stick to tissue, into the shape of a mesh were stacked. The spacers 52 were made high in electric insulation. Furthermore, under the spacers 52, an induction electrode 53 (a metallic member having a lower oxidation/reduction potential) obtained by processing thin titanium wires into the shape of a mesh was disposed, and a protection layer 54 comprising the same material and having the same structure as those of the spacer 52 was disposed at the uppermost face. A disinfectant was applied to the spacer 52 on the side of the induction electrode 53 to form a disinfection layer. A blood component induction cell having this kind of structure was formed. On the outside of the induction electrode 53 of this cell, a polyvinyl chloride tape 56 with an adhesive applied to one side thereof was provided, and the mesh-shaped electrode 51 was short-circuited with the induction electrode 53 at a portion not contacting with blood, thereby forming a first-aid adhesive tape.

The principle of separating and removing the blood components and/or microorganisms from a blood sample in this kind of first-aid adhesive tape will be described below.

More specifically, blood near a wound is polluted with unwanted bacteria from around the wound or the surrounding skin. The polluted blood at the wound passes through the protection layer 54 and penetrates the mesh-shaped electrode 51. As described above, when different kinds of short-circuited metals are opposed with a space therebetween, the blood cell component and/or the unwanted bacteria in the blood move from the metal having a higher oxidation/reduction potential to the metal having a lower oxidation/reduction potential. By using the mesh-shaped electrode 51 as the electrode having a higher oxidation/reduction potential, by using the induction electrode 53 as the electrode having a lower oxidation/reduction potential, and by using the spacers 52 as the space provided between the metals at this time, the unwanted bacteria contained in the blood are induced to the vicinity of the induction electrode 53. As a result, the wound and the surrounding area thereof are disinfected.

The size of the cell used herein differs depending on the portion and size of a wound to be treated and it is preferable that the size should be at least 10 mm×20 mm. The disinfection layer 55 applied to the spacer 52 adjacent to the induction electrode 53 further increases reliability in the effect of bacteria removal.

As a combination of different kinds of metals, a combination of gold and titanium was described and the difference between the oxidation/reduction potentials was about 0.7 V, causing no problem in practice. As combinations other than that described above, a combination of gold and stainless steel and a combination of copper and zinc can also be used.

As a blood sample containing a microorganism, blood (0.5 ml) containing about 1000 cfu/ml of colon bacilli was dropped to the protection layer 54 of the above cell. After this, the flow of the blood and the movement of the colon bacilli were observed. As a result, it was found that the above blood flows into the space formed by the spacers 52 and that the colon bacilli contained in the blood moved toward the induction electrode 53 at a rate of about 2 $\mu$m/sec.

Embodiment 12

An example in which the blood component induction device in accordance with the present invention is applied to a sanitary napkin will be described referring to a drawing.

Figure 14:
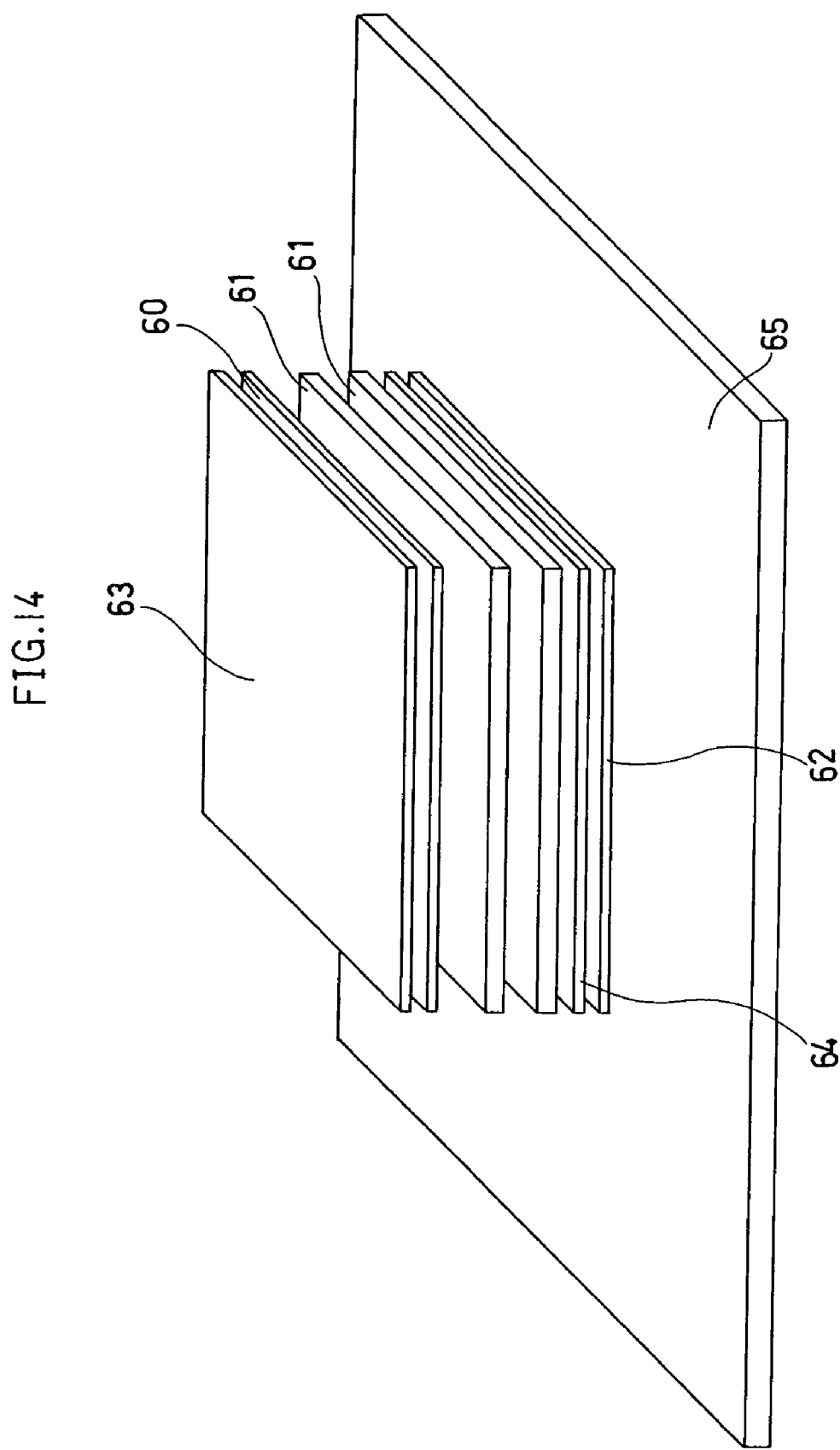
FIG. 14 is a view showing the structure of a sanitary napkin in accordance with another embodiment of the blood component inducting device of the present invention.

FIG. 14 is a view showing the structure of a sanitary napkin in accordance with another embodiment of the blood component induction device of the present invention. As shown in FIG. 14, in the sanitary napkin in accordance with the present invention, a mesh-shaped electrode 60 formed of a mixture of gold wires and synthetic fibers being hard to stick to tissue, each having a diameter of 10 $\mu$m, and spacers 61 (two sheets) obtained by processing fibers, which are hydrophilic and hard to stick to tissue, into the shape of a mesh were stacked. The spacers 61 were made high in electric insulation. Furthermore, under the spacers 61, an induction electrode 62 obtained by processing thin titanium wires into the shape of a mesh was disposed, and a protection layer 63 having a mesh structure and formed of a water-repellent material was provided at the uppermost face. Moreover, a water-absorbing layer 64 formed of a water-absorbing resin was provided on the spacer 61 on the side of the induction electrode 62.

A blood component induction cell having this kind of structure was formed. On the outside of the induction electrode 62 of this cell, a water-impermeable sheet 65 was provided, thereby forming a sanitary napkin.

The principle of separating and removing the blood components and/or microorganisms from a blood sample in this kind of sanitary napkin will be described below.

More specifically, polluted blood passes through the protection layer 63 and penetrates the mesh-shaped electrode 60. As described above, when different kinds of short-circuited metals are opposed with a space therebetween, the blood cell component and/or the unwanted bacteria in the blood move from the metal having a higher oxidation/reduction potential to the metal having a lower oxidation/reduction potential. By using the mesh-shaped electrode 60 as an electrode having a higher oxidation/reduction potential, by using the induction electrode 62 as an electrode having a lower oxidation/reduction potential, and by using the spacers 61 as the space provided between the metals at this time, the unwanted bacteria and/or the blood cell component contained in the blood are induced to the vicinity of the induction electrode 63. As a result, the blood cell components including red blood cells being red in color are separated, and the unwanted bacteria in the blood are removed.

The size of the cell used herein differs depending on the portion and size of a wound to be treated and the size is at least 20 mm×50 mm.

As a combination of different kinds of metals, a combination of gold and titanium was described and the difference between the oxidation/reduction potentials was about 0.7 V, causing no problem in practice. As combinations other than that described above, a combination of gold and stainless steel and a combination of copper and zinc can also be used.

As the material of the electrodes, a metal mesh was taken as an example and described but a similar effect can be obtained even if the material is a metal wire, a porous metal, a metal-foil-processed member or a surface-treated member, the surface of which is formed into a metal layer or film by evaporation or other means. Furthermore, a similar effect can also be obtained even if the above-mentioned metallic member has a porous, mesh or brush form.

The blood component induction device of the present invention can remove the microorganism contained in the blood sample or separate the blood cell component contained therein by using fewer process steps, more easily, in a shorter time and more stably in comparison with a conventional method in which the microorganism contained in the blood sample are disinfected.

Furthermore, when the device is used as a bacteria removing device, an effect of being capable of easily removing the microorganisms included in the blood sample is obtained without using an device such as an external power source.

(iii) Electric Appliance Provided with a Heat Exchanger

Furthermore, the present invention provides an electric appliance provided with a heat exchanger, comprising a metallic member opposed to the heat exchanger with a space therebetween and disposed in condensed dew water flowing from the above-mentioned heat exchanger at a position in contact with the above-mentioned condensed dew water together with the surface of the above-mentioned heat exchanger, and a short-circuit portion for electrically short-circuiting the above-mentioned heat exchanger and the above-mentioned metallic member, wherein the oxidation/reduction potential at the surface of the above-mentioned metallic member differs from that at the surface of the above-mentioned heat exchanger in order to move a microorganism present between the above-mentioned heat exchanger and the above-mentioned opposed member to the above-mentioned metallic member.

In this electric appliance, it is effective that the heat exchanger is formed of aluminum and that the metallic members are formed of metallic titanium.

Furthermore, it is effective that titanium is provided in the condensed dew water passage from the heat exchanger to the drain discharge port, and that drain water is drained between the water passage and the discharge pipe, and electrically insulated from the finally discharged water.

Embodiment 13

The present embodiment will be described referring to FIG. 15.

Figure 15:
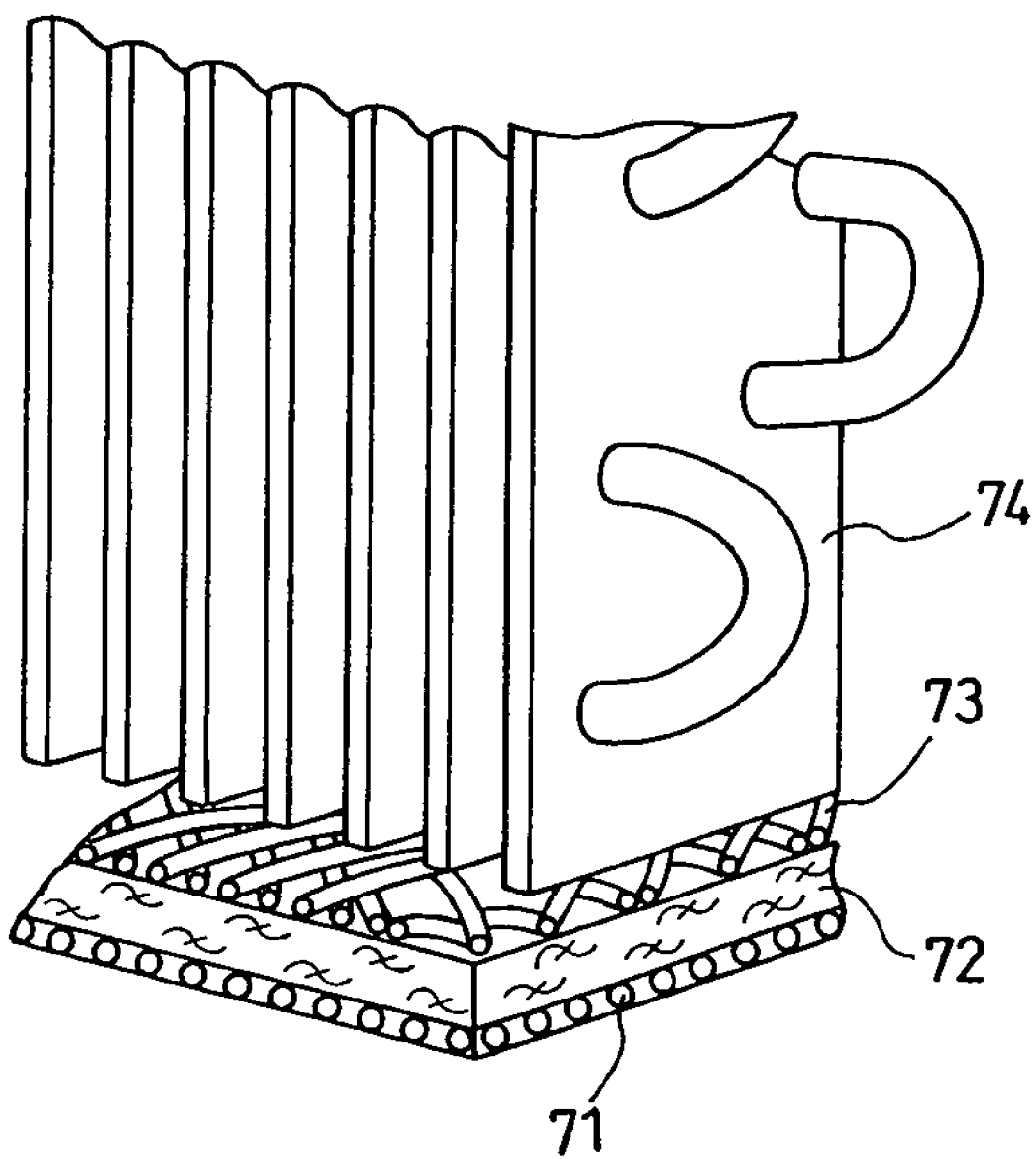
FIG. 15 is a schematic perspective view showing a heat exchanger portion in an air conditioner in accordance with the present invention.

FIG. 15 is a schematic perspective view showing a heat exchanger portion in the air conditioner in accordance with the present invention. A titanium mesh 71 obtained by weaving titanium wires of 50 $\mu$m into a mesh at an opening ratio of 50% used as a metallic member, a non-woven fabric 72 comprising fibers formed of hydrophilic water-permeable paper or the like surface-treated with an antifungal agent and an antimicrobial agent such as thiabenzoimidazole (TBZ), a quaternary ammonium salt and a silver-based antimicrobial agent, and a polypropylene non-woven fabric 73 having a thickness of about 100 $\mu$m used to secure the hydrophilic non-woven fabric 72 to the titanium mesh 71 were stacked. Thus obtained laminate is disposed below the dissipating aluminum fin 74 of the heat exchanger to which the condensed water flows down. The titanium mesh 71 is electrically short-circuited to the dissipating aluminum fin 74, and both are grounded.

In the air conditioner device having the above structure, at least one end thereof makes contact with a condensed water receiving pan (drain pan), and the condensed dew water in the drain pan is electrically connected to the ground level. The condensed dew water discharged from the drain pan is drained to prevent backflow, thereby electrically insulated from a catch basin used as a final discharge destination.

With this structure, the microorganism on the surface of the heat exchanger (aluminum) moves to the surface of the metallic member (titanium) and are adsorbed by the hydrophilic material on the surface of the titanium and, at the same time, the proliferation of the microorganism is prevented by the antifungal and antimicrobial ingredients contained in the material.

In the above-mentioned air conditioner device, the condensed dew water from which microorganism is removed gathers in the drain pan, and is discharged to the catch basin. The microorganism moves to the surface of the metallic member (titanium) since the surface of the heat exchanger (aluminum) is electrically grounded and, however, the microorganism does not move from the catch basin since the catch basin is insulated physically and electrically from the drain pan by water draining.

This phenomenon can be attained without requiring any power source and only when condensed dew water that may allow the microorganism to proliferate is generated and, therefore, the microorganism can be removed from the surface of the aluminum at all times regardless of the operation of the air conditioner.

Furthermore, the air conditioner device having this structure is easily removable from the main unit of the air conditioner, and the hydrophilic non-woven fabric 72 disposed therein is replaceable. When the effectiveness of the antimicrobial and antifungal agents applied to treat the hydrophilic non-woven fabric is lowered and when the microorganism adsorbed and held inside the non-woven fabric is increased, the effect can be restored by replacing the non-woven fabric 72 with a new one.

INDUSTRIAL APPLICABILITY

As described above, the electrochemical device for moving particles covered with a protein in accordance with the present invention can be applied to a microorganism concentration condensing device, a bacteria removing devices, a blood component induction device, an electric appliance provided with a heat exchanger and the like.

Furthermore, the electrochemical device in accordance with the present invention can also be applied to a household electric appliance such as a cooking appliance, a washing machine, a water-purifying device, an ice-making device and a humidifier; a facility product such as a bath, a heat exchanger and an intermediate waterworks; a medical product such as an adhesive tape, a sanitary product and a surgical gauze; a portable drinking water purifying device, a rain water tank and a sewage treatment system.

What is claimed is:

1. An electrochemical device for moving particles covered with a protein comprising:

at least two electrodes and a liquid that contains particles covered with a protein, the liquid being capable of transporting the particles to at least one of the electrodes and the particles being selected from microorganisms and blood cell components, wherein the at least two electrodes oppose each other with a space therebetween, each is at least partially immersed in the liquid and each comprises a metal material having a different oxidation/reduction potential; and a circuit capable of connecting the electrodes outside the liquid to generate a potential difference between the electrodes in a range such that the potential difference does not cause the electrolysis of the liquid, and an electrically insulating structural member through which the liquid moves, the electrically insulating structural member being disposed in the liquid in the space between the at least two electrodes, wherein the device moves the particles in the liquid by electrophoresis in a direction of the electrode having the lower oxidation/reduction potential of the at least two electrodes, wherein the electrode having the higher oxidation/reduction potential of the at least two electrodes has a first structure selected from one of a porous structure, a mesh structure, and a brush structure, another one electrode of the at least two electrodes has a second structure that allows the liquid to flow into the space, provided that where the device has at least three electrodes, the electrode having the second structure does not have the lowest oxidation/reduction potential of the electrodes, and wherein the device gives a condensed concentration of the microorganisms and/or blood cell components in the liquid.

2. The electrochemical device in accordance with claim 1, wherein an introduction portion and a discharge portion for said liquid are provided in a vicinity of the electrode having the higher oxidation/reduction potential relative to the of the at least two electrodes, and a microorganism discharge portion and/or a microorganism adsorption portion are provided in a vicinity of the electrode having the lower oxidation/reduction potential of the at least two electrodes.

3. An electrochemical device for moving particles covered with a protein comprising:

at least two electrodes and a liquid that contains particles covered with a protein, the liquid being capable of transporting the particles to at least one of the electrodes and the particles being selected from microorganisms and blood cell components, wherein the at least two electrodes are at least partially immersed in the liquid and each has a different oxidation/reduction potential; and a circuit generating a potential difference between the electrodes in a range such that the potential difference does not cause the electrolysis of the liquid, wherein the circuit short-circuits the at least two electrodes, and an electrically insulating structural member through which the liquid moves, the electrically insulating structural member being disposed in the liquid in a space between the at least two electrodes, wherein the device moves the particles in the liquid by electrophoresis in a direction of the electrode having the lower oxidation/reduction potential of the at least two electrodes, and wherein the at least one electrode having the higher oxidation/reduction potential of the at least two electrodes has a structure selected from one of a porous structure, a mesh structure, and a brush structure, and the device gives a condensed concentration of the microorganisms and/or blood cell components in the liquid.

* * * * *

UNITED STATES PATENT AND TRADEMARK OFFICE
CERTIFICATE OF CORRECTION

| | | |
|---|---|---|
| PATENT NO. | : 6,972,080 B1 | Page 1 of 1 |
| APPLICATION NO. | : 09/762519 | |
| DATED | : December 6, 2005 | |
| INVENTOR(S) | : Toshikazu Tomioka et al. | |

It is certified that error appears in the above-identified patent and that said Letters Patent is hereby corrected as shown below:

<u>Title Page, Item (56), References Cited, Other Publications, under "Food Batteries", line 2</u>

"Narch 14, 1998" should read -- March 14, 1998 --;

<u>Column 34</u>

Line 18, "another one" should read -- and another --;

<u>Column 34</u>

Line 31, the phrase "relative to the" should be deleted.

Signed and Sealed this

Twenty-third Day of January, 2007

JON W. DUDAS
*Director of the United States Patent and Trademark Office*